United States Patent
Garegnani et al.

(10) Patent No.: US 11,400,093 B2
(45) Date of Patent: Aug. 2, 2022

(54) DEUTERATED ELAGOLIX-LIKE COMPOSITIONS AND METHODS

(71) Applicant: Lupin Inc., Baltimore, MD (US)

(72) Inventors: James Garegnani, Hopewell, NJ (US); Nicholas Hart, Randolph, NJ (US); Richard Holl, Rolla, MO (US)

(73) Assignee: Lupin, Inc., Baltimore, MD (US)

( * ) Notice: Subject to any disclaimer, the term of this patent is extended or adjusted under 35 U.S.C. 154(b) by 0 days.

(21) Appl. No.: 16/741,677

(22) Filed: Jan. 13, 2020

(65) Prior Publication Data

US 2020/0268756 A1 Aug. 27, 2020

Related U.S. Application Data

(60) Provisional application No. 62/792,822, filed on Jan. 15, 2019.

(51) Int. Cl.
| | |
|---|---|
| *C07D 239/46* | (2006.01) |
| *A61K 31/513* | (2006.01) |
| *A61P 15/00* | (2006.01) |
| *A61P 29/00* | (2006.01) |

(52) U.S. Cl.
CPC ............ *A61K 31/513* (2013.01); *A61P 15/00* (2018.01); *A61P 29/00* (2018.01)

(58) Field of Classification Search
CPC ........ A61K 31/513; A61P 15/08; A61P 25/04; A61P 29/00; C07D 239/46
USPC .......................................... 514/274; 544/309
See application file for complete search history.

(56) References Cited

U.S. PATENT DOCUMENTS

| | | | |
|---|---|---|---|
| 6,872,728 | B2 | 3/2005 | Zhu et al. |
| 7,056,927 | B2 | 6/2006 | Guo et al. |
| 7,176,211 | B2 | 2/2007 | Guo et al. |
| 7,179,815 | B2 | 2/2007 | Zhu et al. |
| 7,419,983 | B2 | 9/2008 | Guo et al. |
| 7,462,625 | B2 | 12/2008 | Zhu et al. |
| 2011/0098472 | A1 | 4/2011 | Gallagher |
| 2016/0346255 | A1 | 12/2016 | Kånn |
| 2018/0235963 | A1 | 8/2018 | Goss et al. |

FOREIGN PATENT DOCUMENTS

| | | |
|---|---|---|
| CN | 108129400 | 6/2018 |
| WO | 2017040841 | 3/2017 |
| WO | 2017221144 | 12/2017 |
| WO | 2018198086 | 11/2018 |
| WO | 2018224063 | 12/2018 |
| WO | 2019129310 | 7/2019 |

OTHER PUBLICATIONS

Ezzati, M. et al.: Elagolix, a novel, orally bioavailable GnRH antagonist under investigation for the treatment of endometeriosis-related pain. Woman's Health, vol. 11, pp. 19-28, 2015.*
Orilissa TM (elagolix) Prescribing Information, AbbVie Inc., Jul. 2018.
International Search Report for PCT/US2020/013402 filed Jan. 13, 2020.
Safety Data Sheet—Version 5.0, date Oct. 2, 2019 for Elagolix-d6 Sodium Salt (Major), Catalogue #: E501014; Toronto Research Chemicals.

* cited by examiner

*Primary Examiner* — Charanjit Aulakh
(74) *Attorney, Agent, or Firm* — Transformative Legal, LLC; Len S. Smith; Denise M. Brown

(57) ABSTRACT

New deuterated analogs of elagolix are provided. The novel deuterated elagolix analogs differ from the only previously disclosed deuterated elagolix analogs in structure based on the exclusion of deuterium at certain sites in the compounds and the inclusion of deuterium at other sites. Also provided are new formulations for deuterated elagolix compounds and methods of using such compounds and formulations in the modification of mammalian physiology and especially in the treatment and prevention of a number of diseases and disorders, including endometriosis-associated pain and uterine fibroid conditions.

35 Claims, No Drawings

DEUTERATED ELAGOLIX-LIKE COMPOSITIONS AND METHODS

CROSS-REFERENCE TO RELATED APPLICATIONS

This application claims priority to U.S. Provisional Patent Application 62/792,822, filed Jan. 15, 2019, the entire content of which is hereby incorporated by reference.

FIELD OF THE INVENTION

This disclosure relates to new pharmaceutical compounds, formulations, and novel and inventive methods of using such compounds or formulations for the modulation of physiological conditions in mammals, such as in the treatment of certain conditions.

BACKGROUND

Deuteration of active pharmaceutical ingredients ("APIs") is a known strategy for generating new chemical entities from starting non-deuterated (proteo) analogs. However, despite nearly five decades of reported research and development by leading pharmaceutical companies, including Pfizer and Merck, and work conducted by companies focused on deuteration as a platform for new drug development, such as Concert Pharmaceuticals, while numerous compounds have been described in chemical databases, the number of successfully developed deuterated pharmaceutical compounds remains very limited.

This result in part is because deuteration can result in dozens, scores, or even hundreds (if not thousands) of variants, and many if not most of such chemical variants described for a particular compound, without either experimental data or keen inventive insight, may still result in poor or negative relative efficacy even where in vitro data indicates the presence of such efficacy (e.g., CT-499), and/or may result in undesirable physiochemical properties (such as poor pharmacokinetics compared to the proteo analog, as in the case of Carbazeran and CP-409092), and/or may further or alternatively result in deleterious effects such as undesirable metabolites (e.g., 1,2-dibromoethane and deuterated fludalanine) which may arise due to "metabolic switching". Deuteration changes chemical bonding (length and strength) and can change polarity and other properties/interactions (dipole moment, hydrophobicity, modified acidity/basicity, and Van der Waal's forces). Thus, over the past four decades, despite significant research, the effects of deuterium substitution on the rate of metabolism have only been reported for a very small percentage of approved drugs (see, e.g., Blake, M I et al, J Pharm Sci, 1975, 64:367-91; Foster, A B, Adv Drug Res, 1985, 14: 1-40 ("Foster"); Kushner, D J et al, Can J Physiol Pharmacol, 1999, 79-88; Fisher, M B et al, Curr Opin Drug Discov Devel, 2006, 9: 101-09 ("Fisher")). The results of development of deuterated pharmaceutical agents have been variable and unpredictable. For some compounds deuteration caused decreased metabolic clearance in vivo. For others, there was no change in metabolism. Still others demonstrated increased metabolic clearance. The variability in the effects of deuterization has also led experts to question or dismiss deuterium modification as a viable drug design strategy for inhibiting adverse metabolism (see Foster at p. 35 and Fisher at p. 101).

Furthermore, although numerous APIs have been the subject of deuteration strategies, at both a conceptual and research and development level, there is almost no teaching or disclosure in the art directed to specific deuterated analogs of elagolix (4-({2-[5-(2-fluoro-3-methoxyphenyl)-3-([2-fluoro-6-(trifluoromethyl)phenyl]methyl}-4-methyl-2,6-dioxo-1,2,3,6-tetrahydropyrimidin-1-yl]-1-phenylethyl)amino)butanoic acid), a gonadotropin-releasing hormone (GnRH) receptor antagonist that inhibits endogenous GnRH signaling through competitive binding to the GnRH receptors in the pituitary gland. Such competitive binding results in dose-dependent suppression of luteinizing hormone (LH) and follicle-stimulating hormone (FSH), leading to decreased blood concentrations of the ovarian hormones estradiol and progesterone.

Chinese Patent Application CN108129400A ("the '400 application") appears to be one exception. The '400 application discloses a small number of deuterated derivatives of elagolix, and reports significant increases in the relative bioavailability of such compounds as compared to elagolix.

Elagolix comprises thirty hydrogens. Accordingly, 1,073,741,824 deuterated derivatives of elagolix are possible through deuteration replacements alone (obviously this number would increase significantly if other substitutions are also at issue). However, the '400 application discloses only six specific compounds that exhibit deuteration at two sites in the elagolix structure (and their enantiomers).

The first disclosed site/strategy disclosed in the '400 application focuses on deuteration on all three of the methoxy hydrogens on the ether side chain of the 2-fluoro-1-methoxy-3-methylbenzene ring as shown below (the letter "D" in compounds and formulas presented herein represents deuterium—shading of the tri-deuterium methyl ester group provided for convenience):

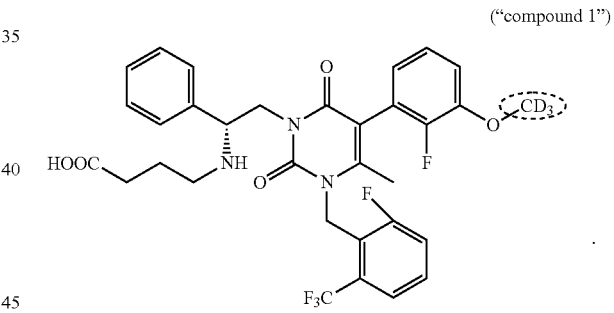

("compound 1")

The other strategy disclosed in the '400 application is directed to deuteration on the methyl side chain (bound to the 6 carbon on the central uracil ring of the compound) as shown by shading below:

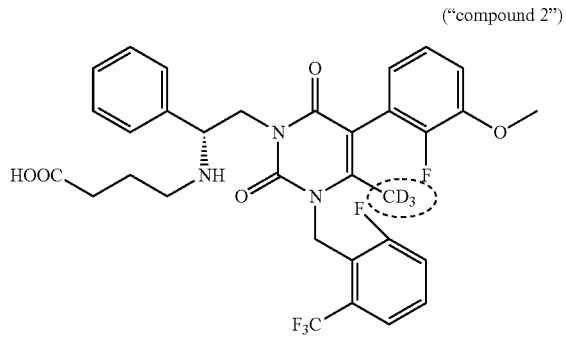 [SMILES: [2H]C([2H])([2H])c1c(-c2cccc(OC)c2F)c(=O)n(C[C@H](NCCCC(=O)O)c2ccccc2)c(=O)n1Cc1c(F)cccc1C(F)(F)F]

("compound 2")

However, the '400 application actually discloses two variations of these deuterated elagolix derivatives, with the second set further including a chlorine replacement of the fluorine normally found on the 2-fluoro-1-methoxy-3-methylbenzene ring of elagolix, as illustratively shown by shading below:

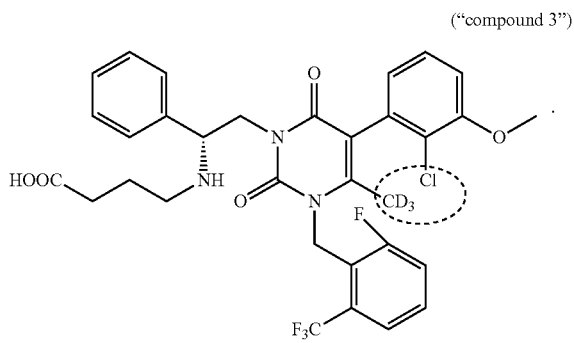 [SMILES: [2H]C([2H])([2H])c1c(-c2cccc(OC)c2Cl)c(=O)n(C[C@H](NCCCC(=O)O)c2ccccc2)c(=O)n1Cc1c(F)cccc1C(F)(F)F]

("compound 3")

The '400 application also discloses compounds having deuteration at both of these sites, with and without the chlorine substitution, as illustrated by the following compound:

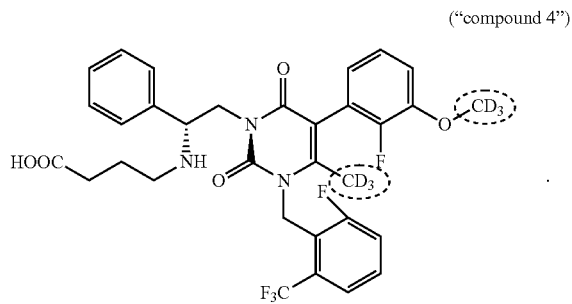

("compound 4")

The '400 application also provides a description of methods of producing the six compounds, formulations comprising such compounds, general methods of using such compounds, and actual use of such compounds in a single animal study and a single in vitro study with compound 2 and compound 4, which showed superior results to compound 1 in vitro and to non-deuterated elagolix in both the in vitro and animal studies.

The disclosure of the '400 application is very limited in terms of the scope of the elagolix compounds described therein, especially in view of the number of potential compounds resulting from deuteration and in view of the potential for such compounds to fail at various points along the path of clinical development. The disclosure of the '400 application is even more limited in terms of methods of using deuterated elagolix compositions and formulations.

DETAILED DESCRIPTION OF THE INVENTION

Disclosed herein are novel deuterated derivatives of elagolix (4-({2-[5-(2-fluoro-3-methoxyphenyl)-3-([2-fluoro-6-(trifluoromethyl)phenyl]methyl}-4-methyl-2,6-dioxo-1,2,3,6-tetrahydropyrimidin-1-yl]-1-phenylethyl)amino)butanoic acid) AND elagolix-like compounds (analogs). Also disclosed herein are new pharmaceutical formulations and other compositions comprising deuterated derivatives of elagolix and elagolix analogs, and inventive methods for the use of deuterated elagolix compounds and analogs, related formulations, and related compositions for the modification of physiological states and/or the treatment or prevention of diseases in mammals, especially in human patients diagnosed as having a condition that is treatable by the administration of such compounds, formulations, and compositions and/or application of the novel methods provided by the invention.

The chemical structure of elagolix (4-({(1R)-2-[5-(2-fluoro-3methoxyphenyl)-3-{[2-fluoro-6-(trifluoromethyl)phenyl]methyl}-4-methyl-2,6-dioxo-3,6dihydropyrimidin-1(2H)-yl]-1-phenylethyl}amino)butanoate) (commercially sold as the sodium salt of this compound under the brand name ORILISSA (marketed by Abbvie)) is shown below with each atom of the compound numbered for use in the discussion of elagolix derivatives herein:

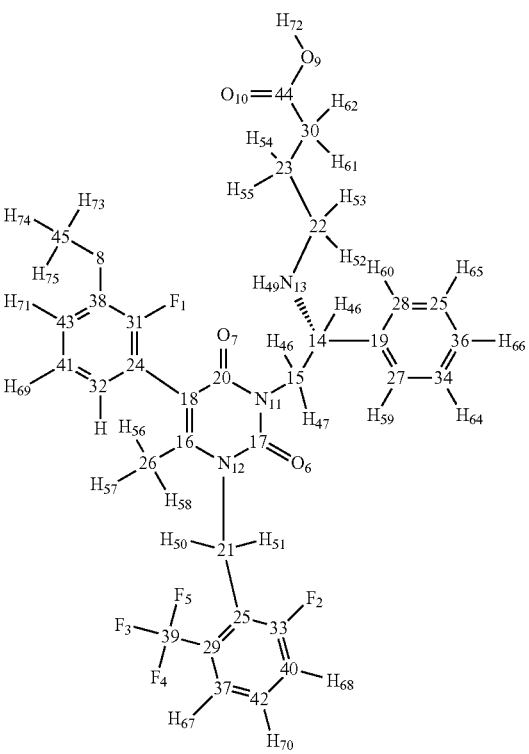

As can be seen above, elagolix comprises four rings, including three aromatic rings and a cycloalkene (uracil) ring (the "A" ring); the three aromatic rings comprising a benzene ring (the "B" ring); two fluorinated rings (a 2-fluoro-1-methoxy-3-methylbenzene ring (the "C" ring) and a 1-fluoro-3-(trifluoromethyl)benzene ring (the "D" ring)). The D ring has a trifluoromethane side chain, the C ring has a methyl ether side chain, the A ring has a methyl side chain, and the linkage between the A and B chains comprises an amino butyric acid (butyrate) side chain. An illustration of elagolix with the rings identified is shown immediately below:

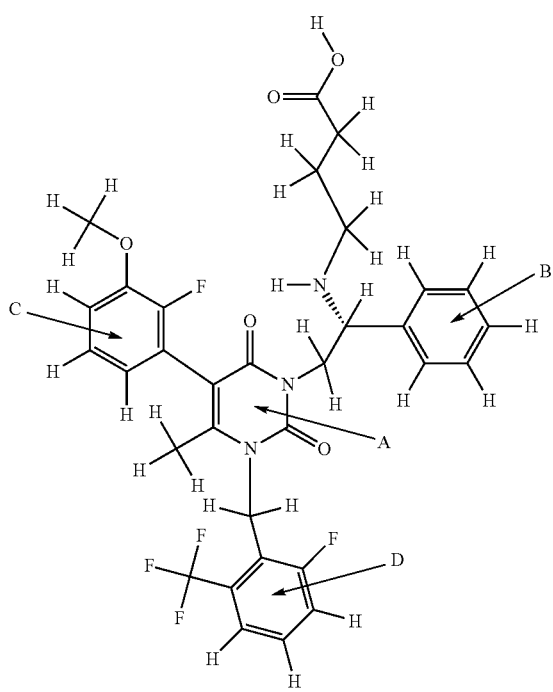

Elagolix and related compounds, formulations, and methods of use are described in U.S. Pat. Nos. 6,872,728; 7,056,927; 7,176,211; 7,179,815; 7,419,983; and 7,462,625. Additional disclosures of relevance to elagolix compositions and applications that may be applicable with respect to the compounds and compositions disclosed herein include International Patent Applications WO/2017/040841, WO/2018/224063, WO/2017/221144, and WO/2018/198086.

Principles of Construction

The following principles should be considered in understanding the disclosure provided herein.

All references, including publications, patent applications, and patents, cited herein, including the patents and patent applications cited above, are hereby incorporated by reference to the same extent as if each reference were individually and specifically indicated to be incorporated by reference and were set forth in its entirety herein. Unless clearly contradicted by context or explicit statement the disclosure of such applications relating to formulations, methods of production, and methods of use of compounds can be combined with the teachings provided herein to provide useful compositions and applications. The citation and incorporation of patent documents herein is done for convenience only and does not reflect any view of the validity, patentability, and/or enforceability of such patent documents.

All headings and sub-headings are used herein for convenience only and should not be construed as limiting the invention in any way.

Recitation of ranges of values herein are merely intended to serve as a shorthand method of referring individually to each separate value falling within the range within an order of magnitude of the order of the range, including the endpoints (e.g., a range of 1-2 is to be interpreted as providing support for 1.0, 1.1, 1.2, 1.3, . . . 1.9, and 2.0; a range of 10-20 is to be interpreted as providing support for 10, 11, 12, 13, . . . 19, and 20), unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate—e.g., disclosure of "about 10" is to be understood as also providing support for 10 exactly). Terms of approximation, such as "about" are used herein where measurements are understood to vary due to measurement issues, e.g., assay limits of detection or variability such as the coefficient of variation of an assay (intra-assay CV), or variability in populations, such as results of clinical studies. The scope of such terms will depend on the context of the element at issue and the understanding of those skilled in the art. In the absence of such guidance in the art through relevant teachings or examples, "about" should be understood as meaning +/−10% of the indicated value(s).

As used herein, the singular form "a", "an", and "the" includes plural references unless clearly indicated otherwise. Use of the term "or" herein is not meant to imply that alternatives are mutually exclusive unless clearly stated or clearly contradicted by context. Thus, in this application, the use of "or" means "and/or" unless expressly stated or understood by one skilled in the art. In the context of a multiple dependent claim or a multiply dependent embodiment or aspect in a set or list of aspects/embodiments, the use of "or" refers back to more than one preceding independent or dependent claim.

All methods described herein can be performed in any suitable order unless otherwise indicated herein or otherwise clearly contradicted by context. Unless clearly indicated or contradicted by context the elements of a composition disclosed herein (e.g., a pharmaceutical formulation) can be formulated in any suitable manner and by any suitable method. Unless otherwise explicitly stated or clearly contradicted by context, any combination of the various elements, steps, components, and/or features of the aspects of the invention described herein, and all possible variations thereof, are to be considered encompassed by the invention.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated. The breadth and scope of the present invention should not be limited by any of the above-described exemplary embodiments, but should be defined only in accordance with the following claims and their equivalents.

The description herein of any aspect or embodiment of the invention using terms such as "comprising", "having," "including," or "containing" with reference to an element, composition, or set of compositions or elements should be interpreted, whether explicitly stated or not, as simultaneously providing support for a similar aspect or embodiment of the invention that "consists of", "consists essentially of", "substantially comprises", "predominately comprises" and "substantially consists of" that particular element, elements, composition, or compositions, unless otherwise stated or clearly contradicted by context (e.g., a composition described herein as comprising a particular element should be understood as also describing a composition consisting of that element, predominately comprising that element, and substantially consisting of that element, unless otherwise stated or clearly contradicted by context).

The phrase "predominately comprises" means that more than one half (i.e., more than 50%) of a relevant type of composition, compound, or other element of a composition is made up of the element at issue (e.g., if a composition is described as "predominately comprising" element/species A, more than 50% of the composition on a molecular and/or weight basis will be made up of element/species A). Unless clearly indicated the term should be understood as providing support for both weight concentration and molecular concentration percentages (e.g., a description of a composition predominately comprising a particular active pharmaceutical ingredient should be understood as providing support for both compositions including over 50% of the API on a molecular species basis and on over 50 wt. % of the API of interest against other elements in the discussion, which based on context may be the entire formulation or a class of chemicals in the formulation). "Substantially comprises" is to be interpreted similarly, but at the level of at least about 1% (of the molecules, weight of the composition, or other element-to-element basis) (and typically at least about 5%, at least about 10%, at least about 15%, and at least about 20%, each of which is to be interpreted as being disclosed in each case where the phrase substantially comprises is used). "Substantially consists of" means at least about 90% (and provides support for at least about 95%, at least about 99%, and at least about 99.9%). Changes to tense of such phrases and similar described phrases used herein (e.g., "predominately comprising, "predominately comprises", or is "predominately comprised of") will maintain the same/similar meaning as any phrase specifically defined or described herein, unless otherwise clearly indicated.

The description of the specific embodiments provided herein will reveal the general nature of the invention such that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Compounds of the Invention

In one facet, the invention described herein provides novel compounds, which are analogs of elagolix, comprising a number of deuterium atoms in place of one or more of the hydrogen atoms typically present in elagolix. Characteristics associated with all, several, and some of the compounds of the invention are provided below. In general, compounds of the invention will be stable, pharmaceutically acceptable, and physiologically (and preferably pharmaceutically) effective. In compounds of the invention, typically less than 50% of the hydrogen atoms in elagolix are substituted with deuterium, and typically 14 or less, 13 or less, 12 or less, 10 or less, or 9 or less of the hydrogens in elagolix are substituted with deuterium. In some cases, as is exemplified several times below, 1-12, more typically 1-9, and often 1-8, 1-7, 1-6, or 1-4 or another range therein (such as 2-12, 3-12, 4-12, 5-12, 6-12, 7-12, 8-12, 2-10, 3-10, 4-10, 5-10, 6-10, 7-10, 8-10, 2-9, 3-9, 4-9, 5-9, 6-9, 7-9, or 8-9 hydrogen atoms in elagolix are substituted with deuterium atoms).

In a first aspect, the invention provides compounds having a structure according to Formula I, shown below (for sake of description of the various embodiments atom numbers are included for each atom included in Formula I):

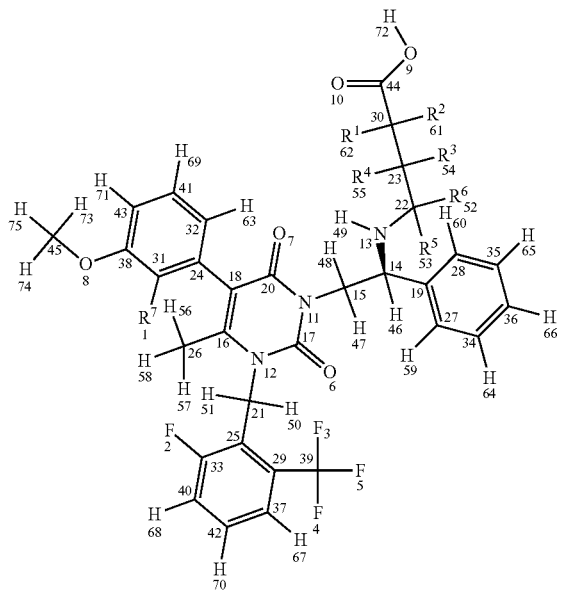

or a stereoisomer or a pharmaceutically acceptable salt thereof, wherein (a) R1, R2, R3, R4, R5, and R6 are either deuterium or hydrogen; (b) R7 is either fluorine or chlorine; and (c) the compound comprises between 1-15 deuterium atoms. Such compounds are typically associated with one or more modulated properties as compared to elagolix (i.e., undeuterated elagolix). Examples of such properties can include a longer half-life, longer retention in a cytochrome P450 isoform assay, reduced hepatic transaminase levels when administered to one or more mammalian subjects, lower and/or less frequent dosage over a treatment period (e.g., of at least one week, at least two weeks, at least one month, at least two months, at least three months and/or up to about 6 months, up to about 9 months, up to about 12 months, up to about 18 months, up to about 24 months, up to about 30 months, or up to about 35 months) without loss of efficacy, and reduced occurrence of adverse events over a treatment period (e.g., as measured in a well-controlled and adequate clinical study of the respective compounds).

In some embodiments the compound will comprise less than 15 deuterium atoms. In one aspect, compounds of the invention contain no more than 14 or no more than 13 deuterium atoms. In another aspect, compounds of the invention contain no more than 12 deuterium atoms. In other aspects, compounds of the invention contain 1-15 deuterium atoms, 1-12 deuterium atoms, 1-11 deuterium atoms, 1-10 deuterium atoms, 1-9 deuterium atoms, 1-8 deuterium atoms, 1-7 deuterium atoms, 1-6 deuterium atoms, 1-5 deuterium atoms, 1-3 deuterium atoms, or 1-2 deuterium atoms. The minimum number of deuterium atoms can be greater than one, such as two, three, four, or five, and the ranges provided in this paragraph can be adjusted accordingly (e.g., in one embodiment the invention comprises 2-15, 2-14, 2-12, 2-10, 2-9, 2-8, 2-6, or 2-3, or 3-15, 3-12, 3-10, 3-9, 3-8, or 3-6 deuterium atoms). As will be reflected in additional exemplary aspects below, in some embodiments at least about 50%, at least about 66.6%, at least about 75%, at least about 80%, or at least about 90% of the deuterium atoms are located in select positions of the compound, such as R1, R2, R3, R4, R5, and R6; H73, H74, and H75; or a combination of R1, R2, R3, R4, R5, and R6 and H73, H74, and H75. In this respect it will be understood that the deuterium atoms of the compound can substitute any suitable hydrogen ("H") in Formula I or the other formulas provided herein. Deuterium atoms also can be added by addition of chemical groups to such a formula to develop a further derived compound. In many cases, most, substantially all, or all of the deuterium atoms will replace a hydrogen that is present in elagolix.

According to one embodiment, at least one of (or only one of) R1, R2, R3, R4, R5, and R6 are deuterium. In certain embodiments, at least two (or only two) of R1, R2, R3, R4, R5, and R6 are deuterium. In more particular aspects, at least three (or three), at least four (or four), or at least five (or five) of R1, R2, R3, R4, R5, and R6 are deuterium. In one embodiment, all of R1, R2, R3, R4, R5, and R6 are deuterium. In a particular embodiment, the only deuterium atoms in the compound are located in one or more of R1, R2, R3, R4, R5, and R6.

According to another embodiment, all of R1, R2, R3, R4, R5, and R6 are hydrogen. In one such embodiment, at least one or at least two of the hydrogens positioned at H73, H74, and H75 are substituted with deuterium. In one such embodiment, only one of H73, H74, and H75 are deuterium. In one embodiment, only two of H73, H74, and H75 are deuterium. In another embodiment, all three of H73, H74, and H75 are deuterium. In some such embodiments, the composition contains no more than nine, no more than seven, no more than six, no more than five, or no more than three deuterium atoms.

The compounds of Formula I comprise at least one chiral/chirality center and, accordingly, can have stereoisomers. In some aspects, it will be understood that such stereoisomers are within the scope of the term "compound." However, in other aspects of the invention, stereoisomers of the compounds of Formula I are excluded from the scope of compounds according to Formula I. Accordingly, the discussion of such compounds and their use herein should be understood as relating to both aspects where stereoisomers are included and excluded.

Unless otherwise stated, when a position, atom, or group is designated specifically as potentially being or comprising "D" or "deuterium" in a formula or structure of the invention, and the disclosure relates to an amount of a composition (e.g., 0.1 microgram (μg or mcg), 1 mcg, 1 mg, 100 mg, 150 mg, 200 mg, 250 mg, or some other amount comprising at least 1,000 of molecules) the position is understood to have deuterium at an abundance that is at least 3000 times greater than the natural abundance of deuterium, which is 0.015% (i.e., at least 45% incorporation of deuterium). In other aspects, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), or at least 6600 (99% deuterium incorporation), or at least 6633.3 (99.5% deuterium incorporation). Of course, in some respects the invention provides the indicated deuterated compounds, per se, as isolated compounds and compositions of such compounds, but typically words such as "compound", when used in the context of compositions of at least 1000s of molecules, will allow for some measurable amount of isotopologue(s) to be present depending on the compound, method of production, methods of purification employed, and similar factors.

The term "isotopologue" (alternatively "isotopolog") refers to a species in which the chemical structure differs from a specific compound of this invention only in the isotopic composition thereof. There may be isotopic variation among the constituent atoms of molecules in a composition of any compound of the invention, such as compositions comprising a compound according to Formula I. Thus, it will be clear to those of skill in the art that a compound represented by a particular chemical structure containing indicated deuterium atoms, when present at any significant amount (e.g., at least 0.1 mcg, at least 1 mcg, at least 10 mcg, at least 1 mg, at least 10 mg, or at least 20 mg) will also typically (unless explicitly otherwise stated) contain lesser amounts of isotopologues having hydrogen atoms at one or more of the designated deuterium positions in that structure. The relative amount of such isotopologues in such a "compound" (i.e., composition of compounds) of this invention will depend upon a number of factors including the isotopic purity of deuterated reagents used to make the compound and the efficiency of incorporation of deuterium in the various synthesis steps used to prepare the compound. However, as set forth above the relative amount of such isotopologues in toto will be less than 55%, and typically less than 49.9% of the compound. In other embodiments, the relative amount of such isotopologues in toto will be less than 47.5% of the "compound" (number of compounds in the composition on a molecular and/or weight basis), less than 40%, less than 32.5%, less than 25%, less than 17.5%, less than 10%, less than 5%, less than 3%, less than 1%, less than 0.5% of the compound, less than 0.2% of the compound, less than 0.1% of the compound, less than 0.05% of the compound, or less than 0.01% of the compound (i.e., the number of compounds in the composition of such isotopologues).

These percentages can also be associated with the terms "average deuteration percentage" (or percent) or "average deuteration rate", indicating the rate or percent of hydrogen atoms in a compound that become or are deuterated with respect to a non-deuterated analog (e.g., elagolix). Thus, for example, the disclosure of deuterated compound compositions having an average deuteration percent of at least 65% means that on average 65% of the compounds comprise deuterium atoms at the one or more sites where deuterium substitution occurs. The invention provides compositions characterized by an average deuteration percentage of at least about 75%, at least about 80%, at least about 85%, at least about 90%, at least about 95%, at least about 99%, at least about 99.5%, and/or at least about 99.9%. In some embodiments all of the chemicals in the composition are deuterated, at least within the relevant levels of detection.

In certain embodiments, the compounds of the present invention may be derivatized, transforming the compound into a compound comprising the chemical structure of a specific compound or of compounds according to a formula of the invention (a "derivative"). According to some embodiments, Thus, the term "compound" for example as used in the description of the compound of Formula I, is intended to encompass any and all acceptable derivatives or compounds resulting from the derivatization of the compound of Formula I. In addition, a formulation of compounds may comprise a compound of the present invention specifically described herein or also or alternatively a derivative of such compound or a mixture of a compound of the present invention and one or more derivatives of the same. The same principle applies to other compounds, beyond that described in Formula I, to include other compounds and formulas disclosed herein. Thus, where a compound is disclosed herein it can be considered that such disclosure also provides support for derivatives thereof. Common derivates include chemicals wherein one or more functional groups are added to promote binding of the compound, change characteristics of the compound (e.g., solubility), increase the weight of the compound, or increase detectability of the compound. Methods of preparing derivatives and derivatization strategies and groups are known in the art.

The compounds of the present invention may generally be utilized as the free acid or free base. Alternatively, the compounds of this invention may be used in the form of acid or base addition salts.

Acid addition salts of the free amino compounds of the present invention may be prepared by methods well known in the art and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Base addition salts include those salts that form with a carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like).

The compounds of Formula I and other formulas described herein will typically be present as salts of the described compound and typically such salts will be "pharmaceutically acceptable." Thus, the term "pharmaceutically acceptable salt" of Formula I is intended to encompass any and all acceptable salt forms of the compounds encompassed by this Formula (structure). The same principle applies to other compounds and formulas disclosed herein.

The term "pharmaceutically acceptable," as used herein (e.g., with respect to compositions of the invention, salts, and other excipients, diluents, carriers, etc.), refers to a component that is, within the scope of sound medical and/or pharmaceutical judgment, suitable for use in contact with one or more tissues of humans and other mammals without undue toxicity, irritation, allergic response and the like, and are commensurate with a reasonable benefit/risk ratio.

A "pharmaceutically acceptable salt" means any nontoxic salt that, upon administration to a recipient, is capable of providing, either directly or indirectly, a compound of this invention. A "pharmaceutically acceptable counterion" is an ionic portion of a salt that is not toxic when released from the salt upon administration to a recipient. A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, parabromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

A particularly advantageous salt in the context of the compounds of Formula I and other compounds disclosed herein is the sodium salt of such compounds.

It will be understood that when a compound is discussed herein that the disclosure also includes, whether stated or not, the compound in a suitable salt form.

The compositions and formulations of the invention are typically and advantageously stable. The term "stable" with respect to "stable compounds" and "stable formulations" as used herein, refers to compounds and compositions/formulations which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, and/or treating a disease or condition responsive to therapeutic agents).

In one aspect, the invention provides compounds according to Formula I wherein R7 of Formula I is fluorine. According to a more particular aspect, the invention provides compounds, formulations, and methods of using the same wherein the composition (formula) defining the compound lacks any chlorine. According to other embodiments, compounds of the invention also or alternatively can be characterized in that at least one, at least two, or all three of the hydrogens in positions H56, H57, and H58 of Formula I (or a corresponding formula presented elsewhere herein, e.g., any one of Formulas 2-30), are maintained (i.e., not substituted with deuterium). Thus, for example, the invention provides compounds in which at least one, at least two, at least three, at least four, or all of R1, R2, R3, R4, R5, and R6 are deuterium, but in which H56, H57, and H58 are maintained as hydrogens. In another example of such an aspect, the invention provides compounds in which one or two, and in other aspects all three, of H73, H74, and H75 are substituted with deuterium, but in which H56, H57, and H58 are maintained as hydrogens. And in yet another embodiment, the invention provides compounds in which at least one of R1, R2, R3, R4, R5, and R6 are deuterium, at least one of H73, H74, and H75 are substituted with hydrogen, and H56, H57, and H58 are maintained as hydrogens.

In other embodiments, as further reflected below, one, two, or all three of H56, H57, and H58 of a compound according to one of the formulas/structures provided herein are substituted with deuterium, alone or in combination with other deuterium substitutions (e.g., at least one of H73, H74, and H75 and/or in at least one of R1, R2, R3, R4, R5, and R6 are deuterium)

In one aspect, the invention provides compounds according to Formula I, wherein 1-12, typically 1-10, and more typically 1-9 of the hydrogen atoms in elagolix have been substituted with a deuterium. In a particular aspect, at least about 65%, more typically at least about 75%, and still more typically at least about 90% of the deuterium atoms in the compound of Formula I are located at positions R1, R2, R3, R4, R5, or R6 or substitute a hydrogen at position H56, H57, H58, H73, H74, or H75. In still a more particular aspect, all of the deuterium atoms in the compound of Formula I are located in a position selected from R1, R2, R3, R4, R5, and R6 and/or substitute a hydrogen at position selected from H56, H57, H58, H73, H74, and H75. According to embodiments, no more than two of H73, H74, and H75 are substituted with deuterium. According to further embodiments, no more than one of H73, H74, and H75 are substituted with deuterium.

In other aspects, the invention provides pharmaceutical formulations comprising such compounds and methods of using such compounds (according to Formula I and any of the above-described variations thereof) to modulate the physiology of mammalian hosts, such as in treating or preventing one or more conditions associated with such modulation (e.g., treatment of endometriosis-associated pain in a human female patient). The details of such aspects of the invention are provided elsewhere herein.

A representation of some of the compounds provided by the preceding disclosure is provided here as Formula II:

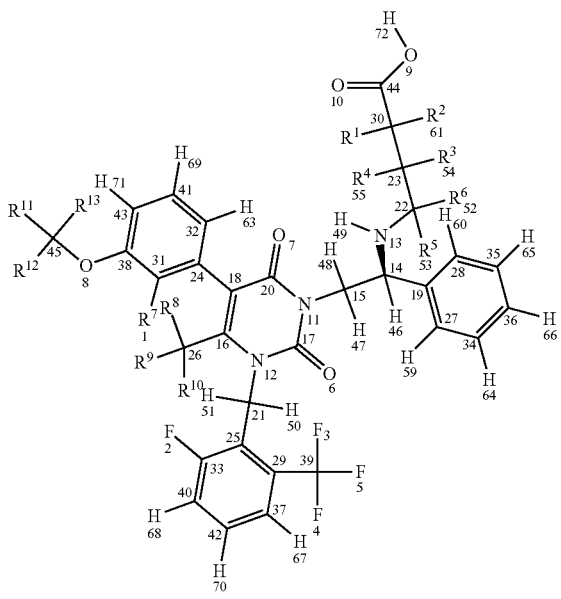

wherein R1-R6 and R8-R13 are deuterium or hydrogen ("Formula II" or "Formula 2"). Typically, in compounds according to Formula II, either 1-2, only one, or none of R11-R13 are deuterium. Also or alternatively, Formula II compounds can be characterized in some embodiments by only two, only one, or none of R8-R10 being deuterium. In other aspects, the invention provides pharmaceutical formulations comprising such compounds (according to Formula 2) and methods of using such compounds to modulate the physiology of mammalian hosts, such as in treating or preventing one or more conditions associated with such modulation (e.g., treatment of endometriosis-associated pain in a human female patient). The details of such aspects of the invention are provided elsewhere herein.

In some embodiments, at least about 65%, at least about 70%, at least about 80%, or at least about 90% of the 1-12, 1-10, or 1-9 deuterium atoms in compounds according to Formula I and/or Formula II (to the extent sensible) are located at positions R, R2, R3, R4, R5, or R6 or substitute a hydrogen at position H56, H57, or H58 (when considering such embodiments with respect to Formula H the corresponding R groups at these positions can be considered to be modified by the relevant disclosure). According to embodiments, the hydrogens at positions H73, H74, and H75 are maintained in such compounds of Formula I or Formula II. According to more particular embodiments, all of the 1-9 deuterium atoms in the compounds of Formula I or Formula II are located at positions R1, R2, R3, R4, R5, or R6 or substitute a hydrogen at position H56, H57, or H58. In other aspects, the invention provides pharmaceutical formulations comprising such compounds (according to Formula 1 or Formula 2 and as modified by any of the variations thereof discussed above) and methods of using such compounds to modulate the physiology of mammalian hosts, such as in treating or preventing one or more conditions associated with such modulation (e.g., treatment of endometriosis-associated pain in a human female patient). The details of such aspects of the invention are provided elsewhere herein.

According to embodiments, the invention provides compounds according to Formula I (or Formula II), modified by any of the preceding or following more particular characteristics/limitations, wherein the compounds comprise at least two deuterium atoms. In some embodiments the invention provides compounds according to Formula I wherein no more than five atoms are deuterium. Still other aspects the invention provides compounds that comprise at least three deuterium atoms, at least four deuterium atoms, and at least five deuterium atoms, or precisely 2, 3, 4, or 5 deuterium atoms. In a particular embodiment the invention provides compounds according to Formula I or Formula II wherein the composition comprises at least two (or two) (e.g., 2-5), at least three (or three) (e.g., 3-5), or at least four (or four) (e.g., 4-5), or at least five (or five) deuterium atoms, wherein at least one of the deuterium atoms substitute a hydrogen at position H56, H57, or H58 and, also or alternatively, least two (or two) (or at least three (or three) or at least four (or four) of R1, R2, R3, R4, R5, and R6 are deuterium. According to some aspects, no more than two of H56, H57, and H58 in any of such compounds are substituted with deuterium. In other aspects, the invention provides pharmaceutical formulations comprising such compounds (according to Formula 1 or Formula 2 and as modified by any of the variations thereof discussed above) and methods of using such compounds to modulate the physiology of mammalian hosts, such as in treating or preventing one or more conditions associated with such modulation (e.g., treatment of endometriosis-associated pain in a human female patient). The details of such aspects of the invention are provided elsewhere herein.

In one embodiment, the invention provides compositions according to Formula III shown below:

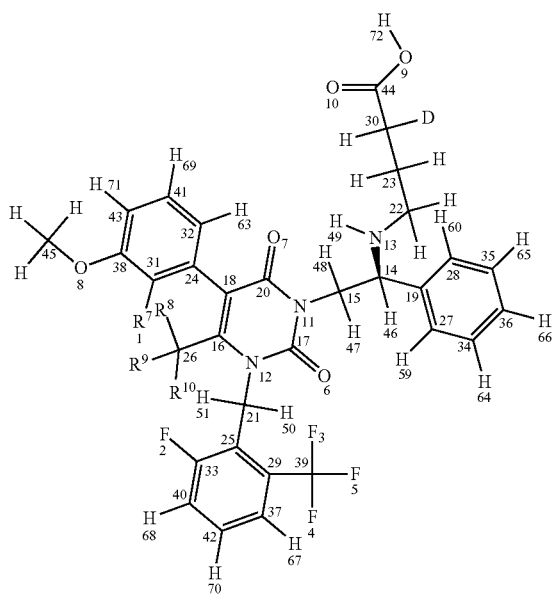

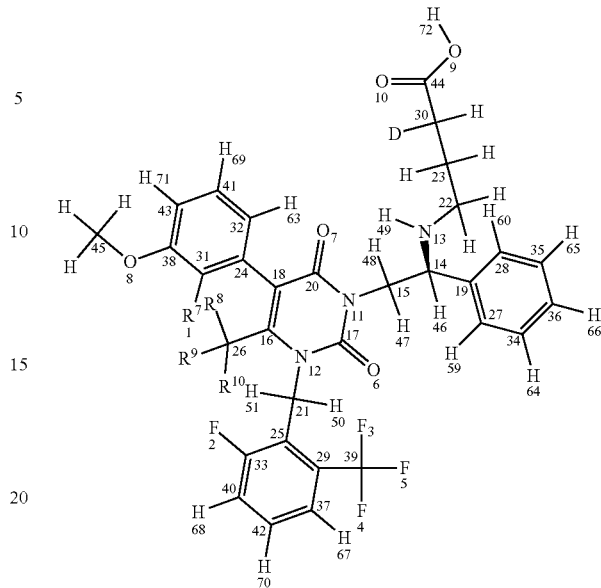

wherein R7 is chlorine or fluorine, typically fluorine, and R8, R9, and R10 are hydrogen or deuterium, typically only one or two of R8, R9, and R10 are deuterium ("Formula IV" or "Formula 4"). In other aspects, the invention provides pharmaceutical formulations comprising such compounds (according to Formula 4) and methods of using such compounds to modulate the physiology of mammalian hosts, such as in treating or preventing one or more conditions associated with such modulation (e.g., treatment of endometriosis-associated pain in a human female patient). The details of such aspects of the invention are provided elsewhere herein.

In still another exemplary aspect, compounds according to Formula V as shown below are provided:

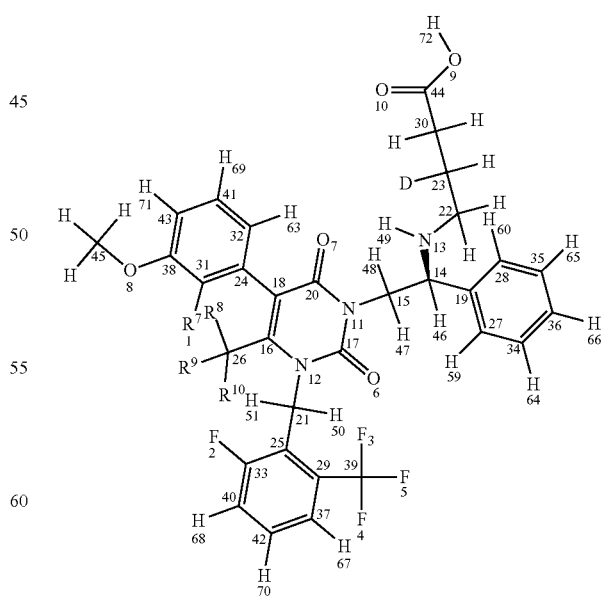

wherein R7 is chlorine or fluorine, typically fluorine, and R8, R9, and R10 are either hydrogen or deuterium, wherein typically only one or two of R8, R9, and R10 are deuterium ("Formula III" or "Formula 3"). In other aspects, the invention provides pharmaceutical formulations comprising such compounds (according to Formula 3) and methods of using such compounds to modulate the physiology of mammalian hosts, such as in treating or preventing one or more conditions associated with such modulation (e.g., treatment of endometriosis-associated pain in a human female patient). The details of such aspects of the invention are provided elsewhere herein.

In another exemplary aspect, the invention provides compounds according to Formula IV as shown below:

wherein R7 is chlorine or fluorine, typically fluorine, and R8, R9, and R10 are either hydrogen or deuterium, and wherein typically only one or two of R8, R9, and R10 are deuterium ("Formula V" or "Formula 5"). In other aspects, the invention provides pharmaceutical formulations comprising such compounds and methods of using such compounds (according to Formula 5) to modulate the physiology of mammalian hosts, such as in treating or preventing one or more conditions associated with such modulation (e.g., treatment of endometriosis-associated pain in a human female patient). The details of such aspects of the invention are provided elsewhere herein.

An additional exemplary aspect of the invention is embodied in compounds according to Formula VI, as shown below:

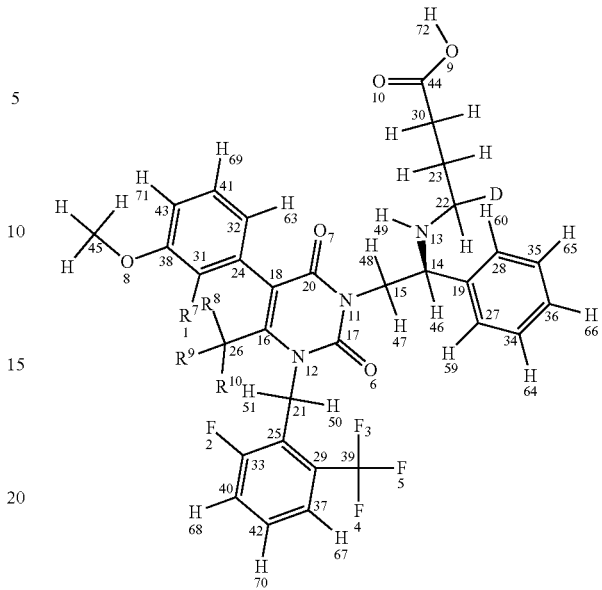

wherein R7 is chlorine or fluorine, typically fluorine, and R8, R9, and R10 are either hydrogen or deuterium, and wherein typically only one or two of R8, R9, and R10 are deuterium ("Formula VII" or "Formula 7"). In other aspects, the invention provides pharmaceutical formulations comprising such compounds (according to Formula 7) and methods of using such compounds to modulate the physiology of mammalian hosts, such as in treating or preventing one or more conditions associated with such modulation (e.g., treatment of endometriosis-associated pain in a human female patient). The details of such aspects of the invention are provided elsewhere herein.

Still another exemplary aspect of the invention is embodied in compounds according to Formula VIII, as shown below:

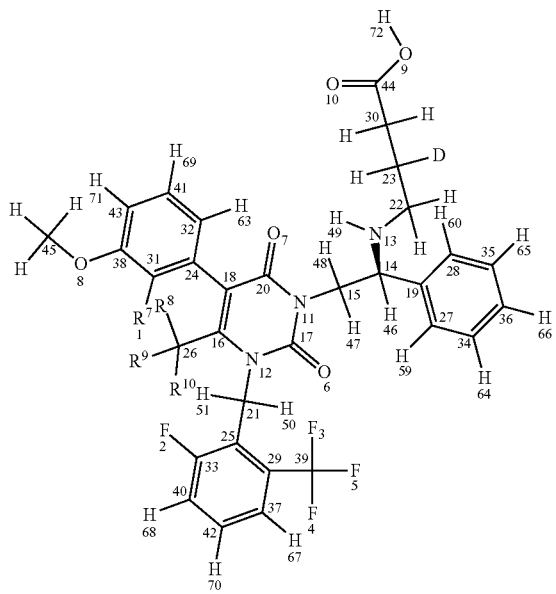

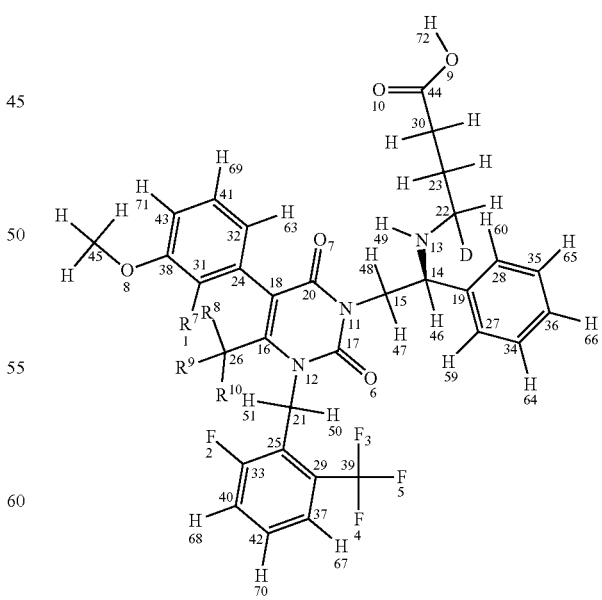

wherein R7 is chlorine or fluorine, typically fluorine, and R8, R9, and R10 are either hydrogen or deuterium, and wherein typically only one or two of R8, R9, and R10 are deuterium ("Formula VI" or "Formula 6"). In other aspects, the invention provides pharmaceutical formulations comprising such compounds (according to Formula 6) and methods of using such compounds to modulate the physiology of mammalian hosts, such as in treating or preventing one or more conditions associated with such modulation (e.g., treatment of endometriosis-associated pain in a human female patient). The details of such aspects of the invention are provided elsewhere herein.

In yet another aspect, the invention provides compositions according to Formula VII:

wherein R7 is chlorine or fluorine, typically fluorine, and R8, R9, and R10 are either hydrogen or deuterium, and wherein typically only 1 or 2 of R8, R9, and R10 are deuterium ("Formula VIII" or "Formula 8"). In other aspects, the invention provides pharmaceutical formulations comprising such compounds (according to Formula 8) and methods of using such compounds to modulate the physiology of mammalian hosts, such as in treating or preventing one or more conditions associated with such modulation (e.g., treatment of endometriosis-associated pain in a human female patient). The details of such aspects of the invention are provided elsewhere herein.

In still another illustrative aspect the invention provides compounds according to Formula IX shown here:

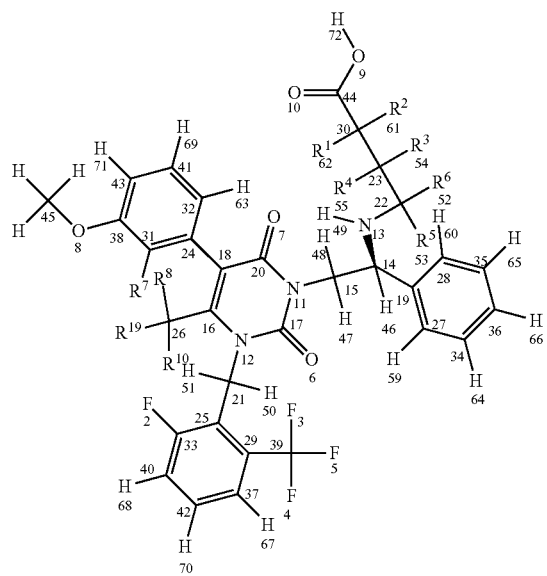

wherein R7 is chlorine or fluorine, typically fluorine; two, three, four, or five (typically 2-4, and usually 2-3) of R1, R2, R3, R4, R5, and R6 are deuterium, with the remainder being hydrogen; and zero, one, or two of R8, R9, and R10 are deuterium, with the other members of R8, R9, and R10 being hydrogen ("Formula IX" or "Formula 9"). According to more particular embodiments, compounds according to Formula IX are provided wherein two of R1-R6 are deuterium and 0-2, 0, 1, or 2 of R8-R10 are deuterium. According to other particular embodiments, compounds according to Formula IX are provided wherein 3-5, typically 3-4, and commonly 3 of R1-R6 are deuterium (with the remainder of the group being hydrogen) and 0, 1, or 2 of R8-R10 are deuterium, with the remainder of R8-R10 being hydrogen. In other aspects, the invention provides pharmaceutical formulations comprising such compounds (according to Formula IX, including any of the indicated possible variations thereof) and methods of using such compounds to modulate the physiology of mammalian hosts, such as in treating or preventing one or more conditions associated with such modulation (e.g., treatment of endometriosis-associated pain in a human female patient). The details of such aspects of the invention are provided elsewhere herein.

Additional exemplary compounds of the invention are provided in Table I, below:

TABLE 1

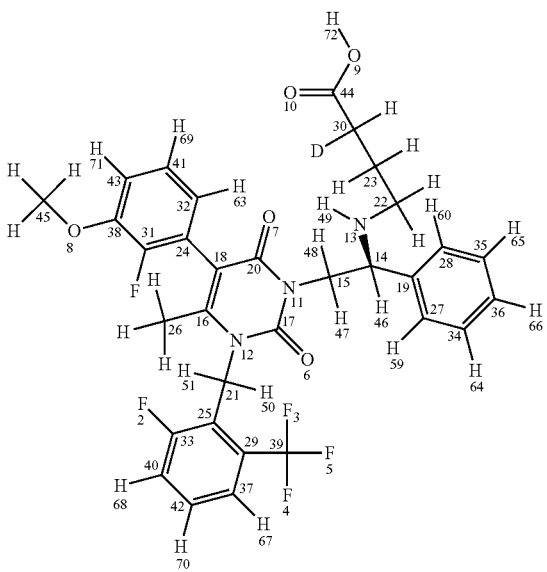 [SMILES: [2H]C(CC([2H])([2H])C(=O)O)N[C@@H](Cn1c(=O)c(-c2cccc(OC)c2F)c(C)n(Cc2c(F)cccc2C(F)(F)F)c1=O)c1ccccc1]

Formula 11

TABLE 1-continued
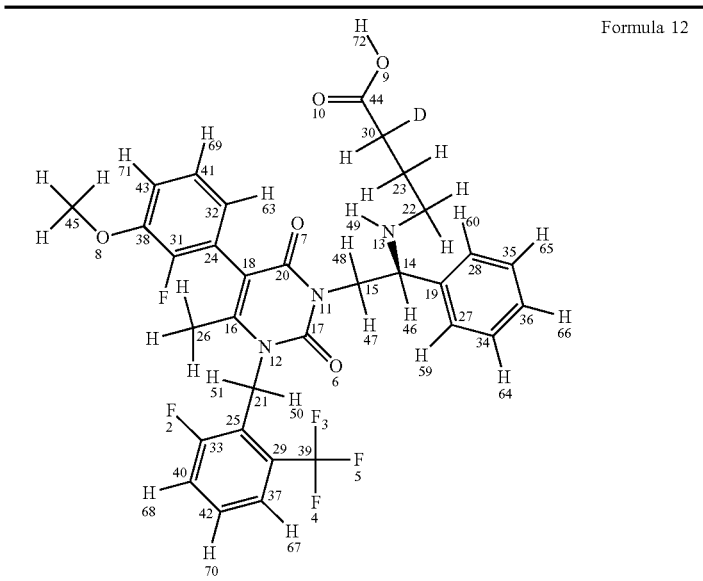
Formula 12
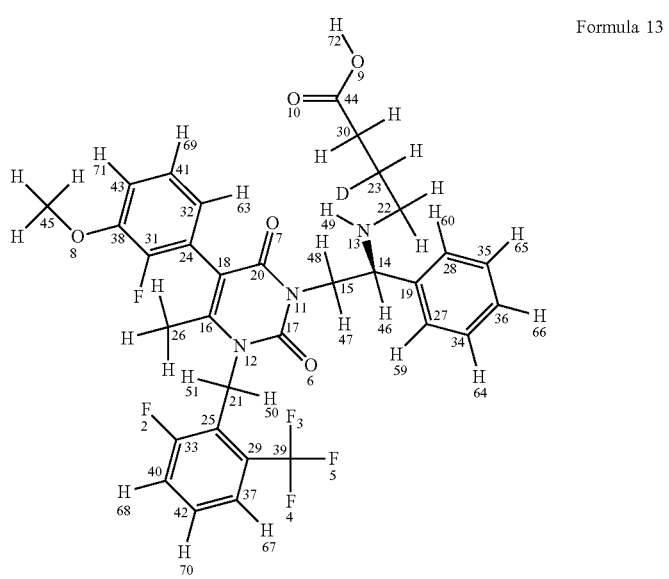
Formula 13

TABLE 1-continued
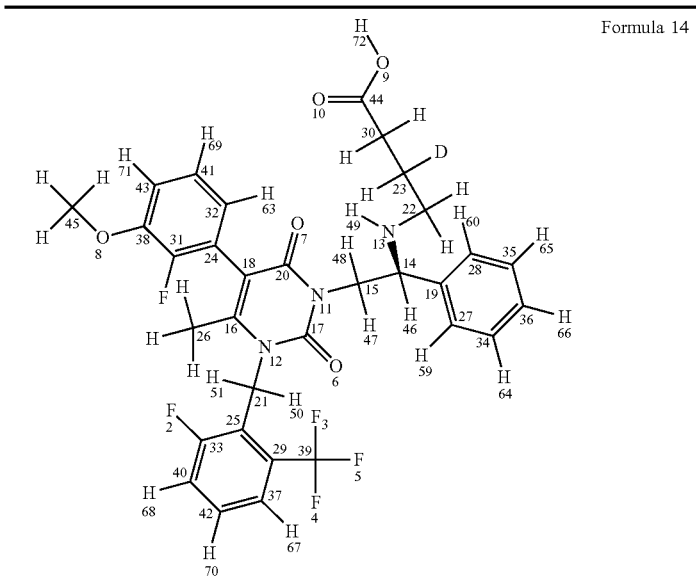
Formula 14
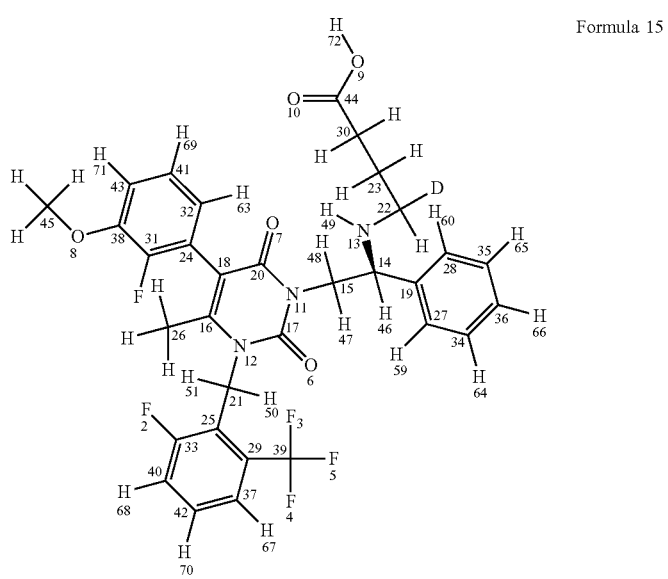
Formula 15

TABLE 1-continued
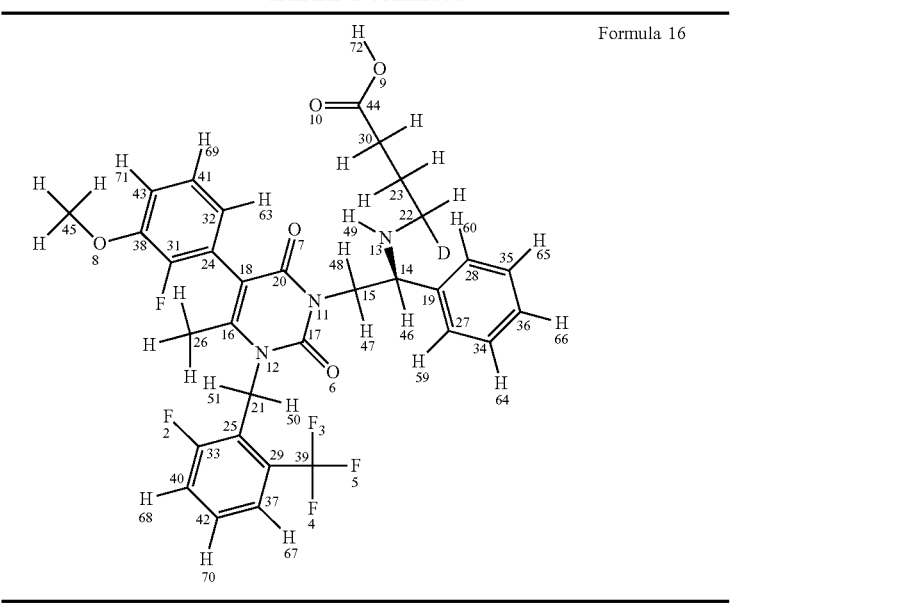
Formula 16
Still, further illustrative compounds of the invention are provided in Table 2, below—
TABLE 2
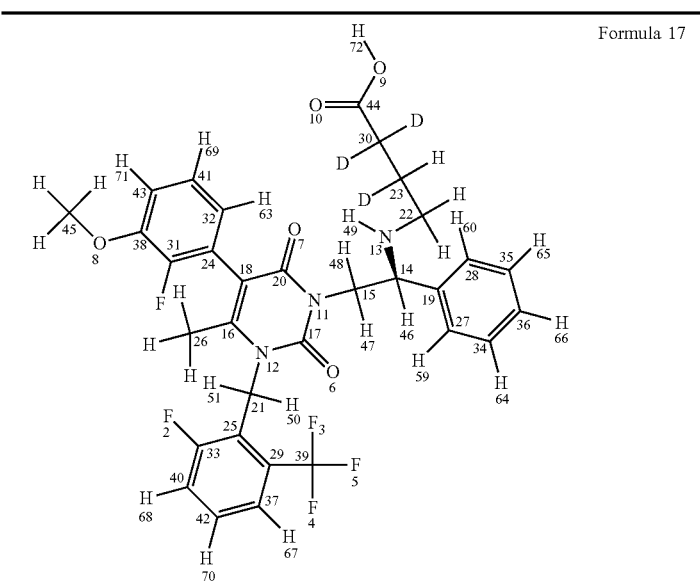
Formula 17

TABLE 2-continued
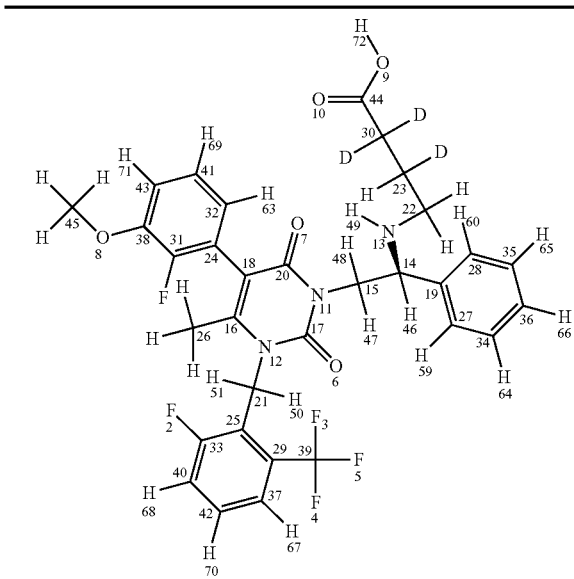
Formula 18
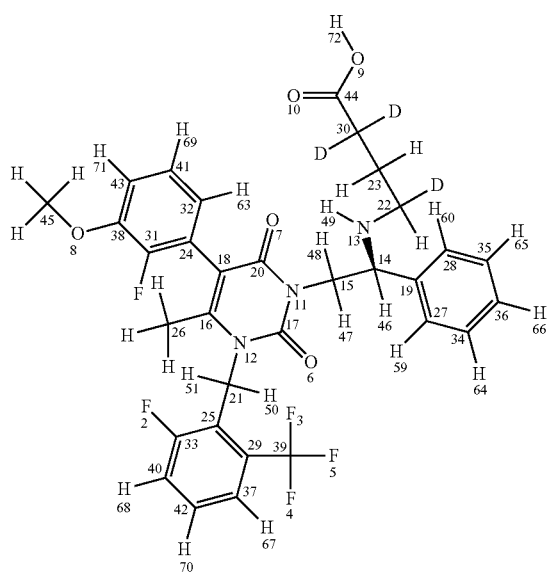
Formula 19

US 11,400,093 B2
TABLE 2-continued
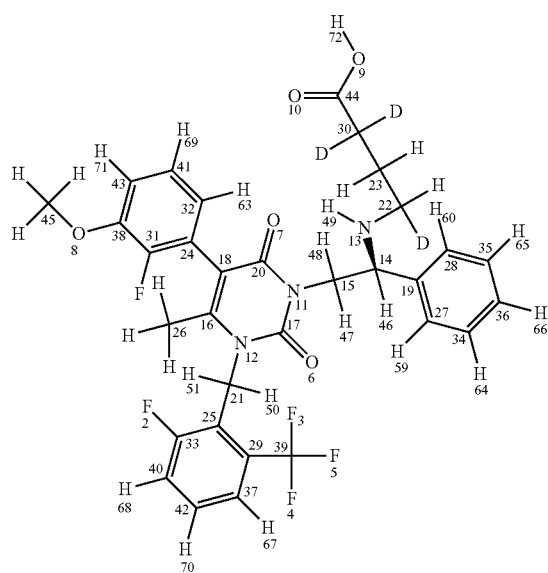 [SMILES: [2H]C(CC([2H])([2H])C(=O)O)N[C@@H](Cn1c(=O)c(-c2cccc(OC)c2F)c(C)n(Cc2c(F)cccc2C(F)(F)F)c1=O)c1ccccc1]
Formula 20
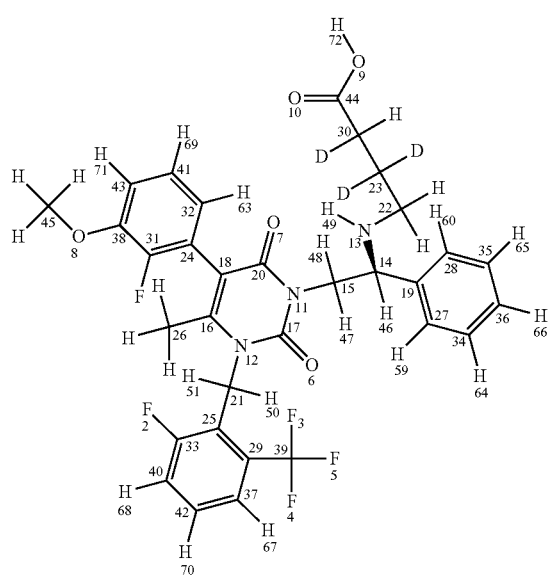
Formula 21

TABLE 2-continued
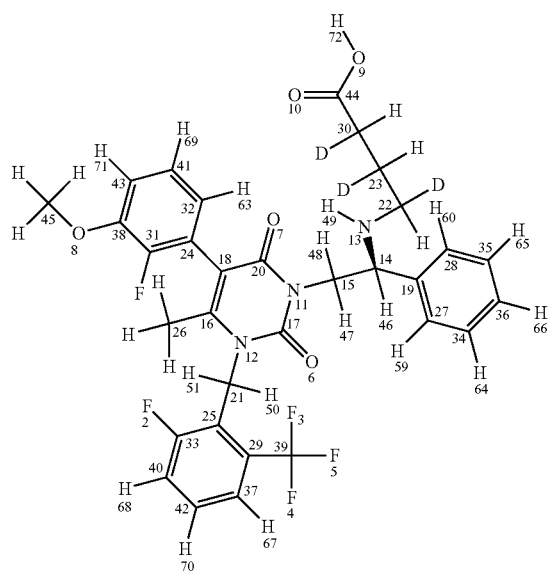
Formula 22
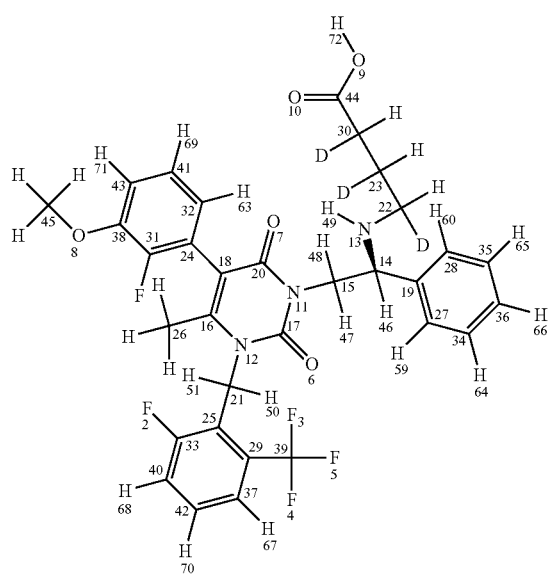 [SMILES: [2H]C(N[C@@H](Cn1c(=O)c(-c2cccc(OC)c2F)c(C)n(Cc2c(F)cccc2C(F)(F)F)c1=O)c1ccccc1)C([2H])([2H])CC(=O)O]
Formula 23

TABLE 2-continued
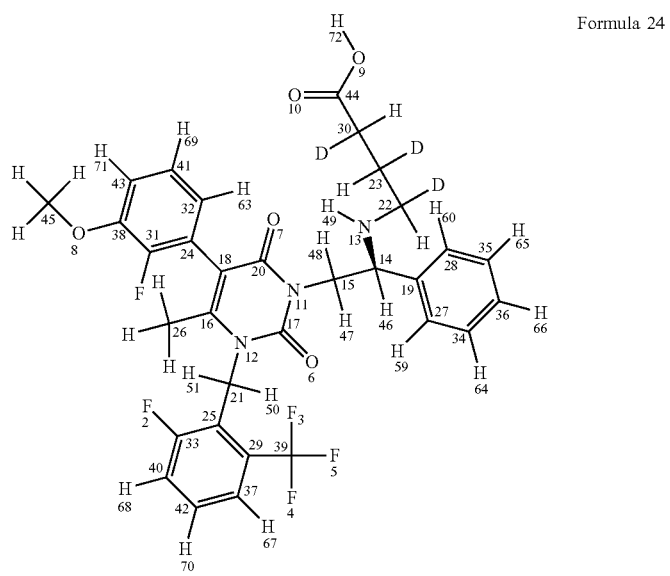
Formula 24
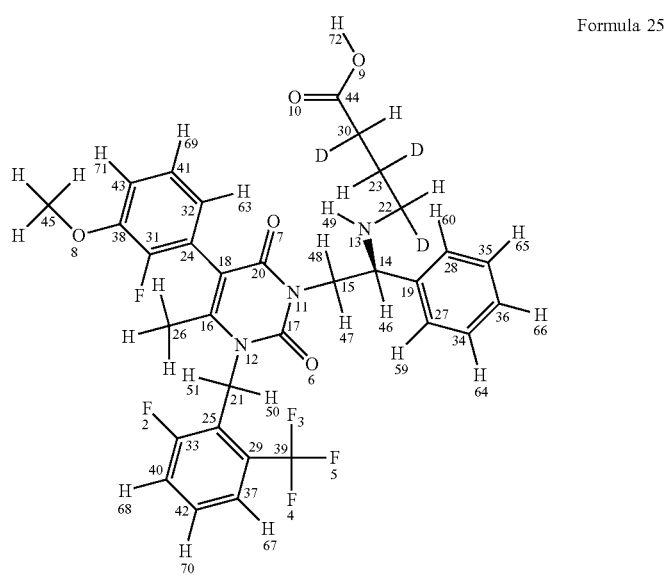
Formula 25

TABLE 2-continued
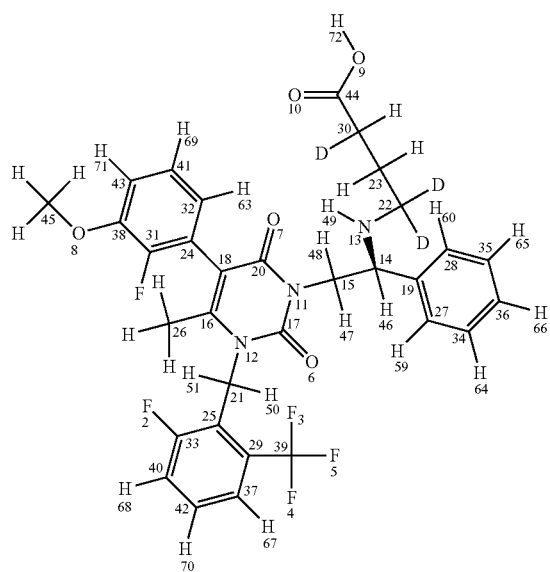 [SMILES: [2H]C(CC(=O)O)C([2H])([2H])N[C@@H](Cn1c(=O)c(-c2cccc(OC)c2F)c(C)n(Cc2c(F)cccc2C(F)(F)F)c1=O)c1ccccc1]
Formula 26
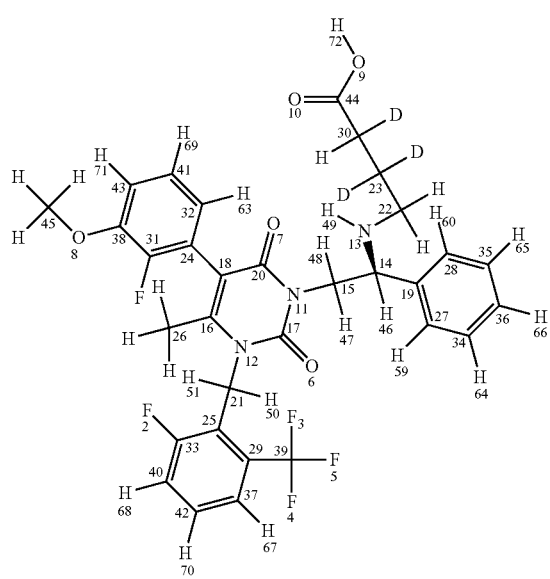
Formula 27

TABLE 2-continued
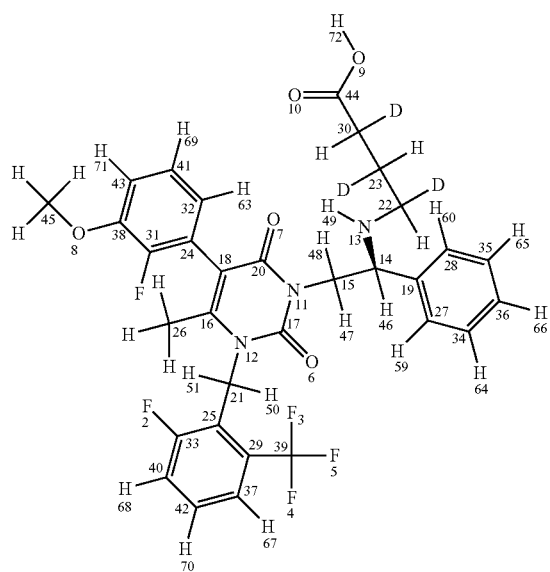 [SMILES: [2H]C(CC(=O)O)C([2H])([2H])N[C@@H](Cn1c(=O)c(-c2cccc(OC)c2F)c(C)n(Cc2c(F)cccc2C(F)(F)F)c1=O)c1ccccc1]
Formula 28
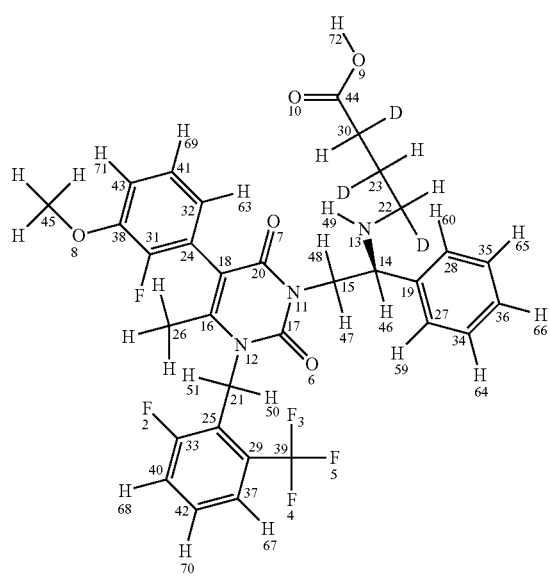
Formula 29

TABLE 2-continued
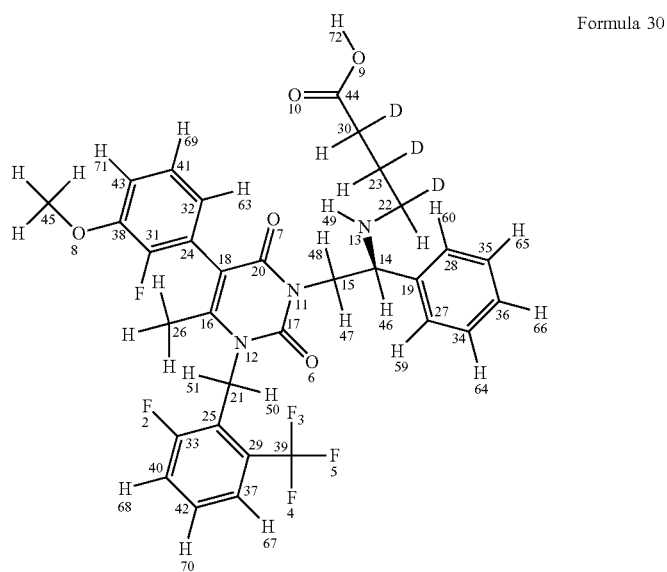
Formula 30
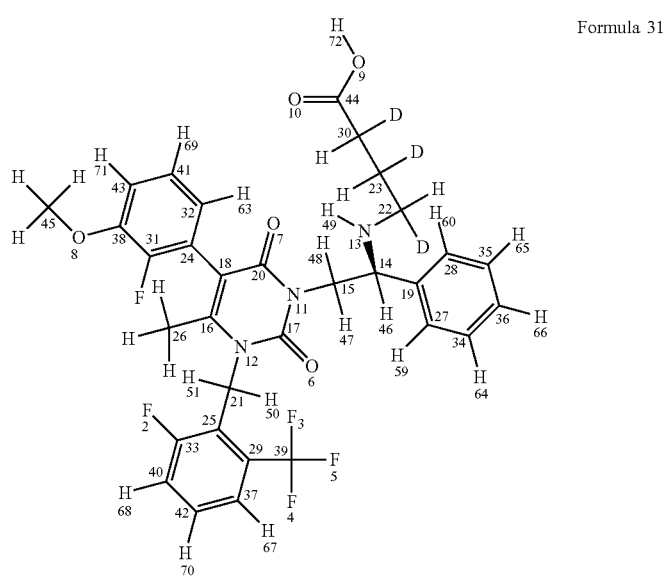
Formula 31

TABLE 2-continued
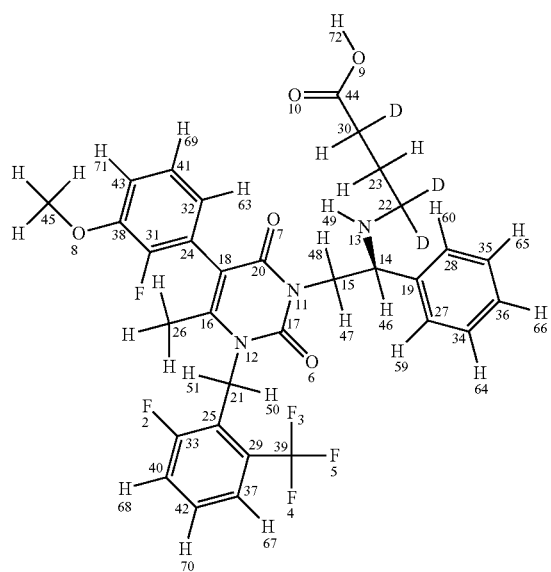
Formula 32
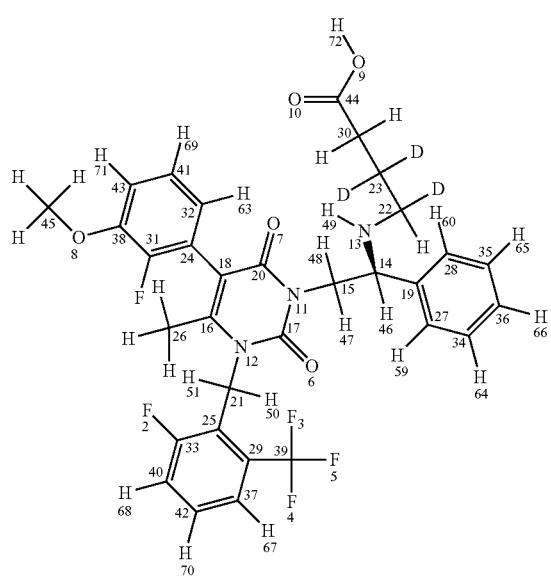
Formula 33

TABLE 2-continued
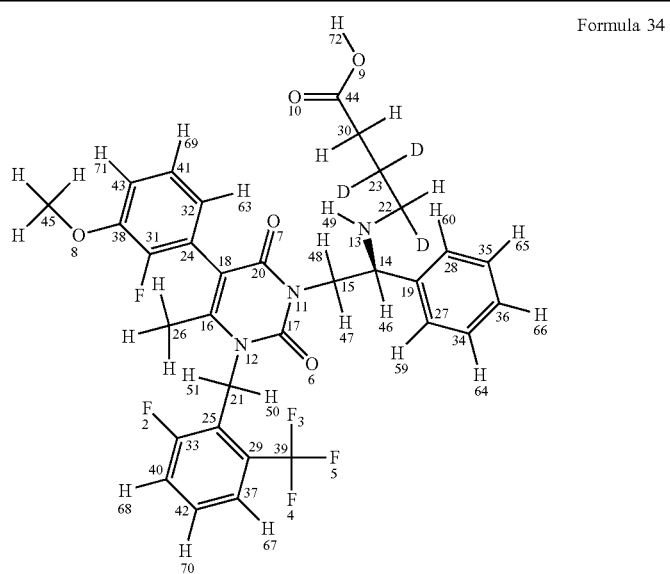
Formula 34
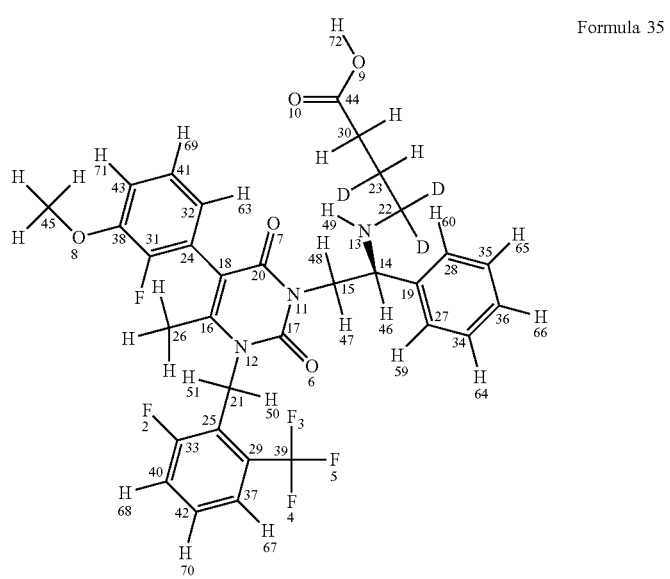
Formula 35

TABLE 2-continued

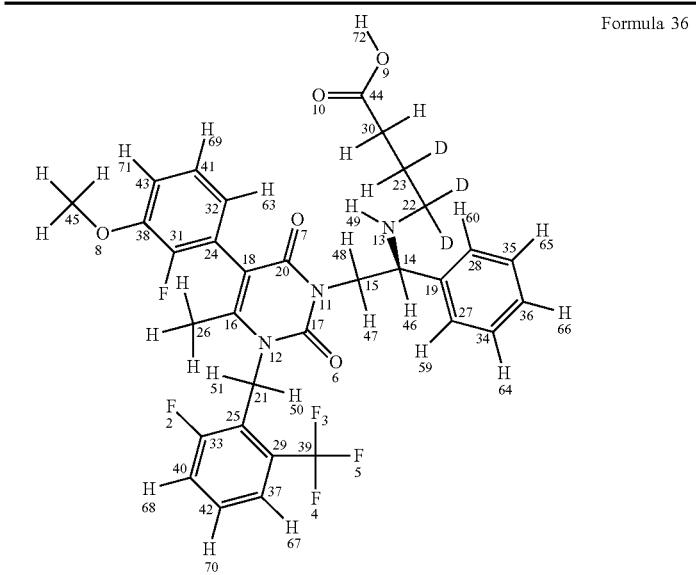

Formula 36

In other aspects, the invention provides pharmaceutical formulations comprising such compounds (according to any one of formulas 11-36) and methods of using such compounds to modulate the physiology of mammalian hosts, such as in treating or preventing one or more conditions associated with such modulation (e.g., treatment of endometriosis-associated pain in a human female patient). The details of such aspects of the invention are provided elsewhere herein.

In other embodiments, compounds according to Formula I or Formula II comprising six or more deuterium atoms, typically 6-12 deuterium atoms, and more typically 6-10 deuterium atoms or 6-9 deuterium atoms (e.g., 6-7 or 6-8 deuterium atoms) also are provided. According to embodiments, at least three, at least four, or at least five of R1, R2, R3, R4, R5, and R6 are deuterium in such compounds. According to embodiments 1, 2, or 3 of H56, H57, and H58 (or the corresponding R groups at the same positions in Formula II) are deuterium, but typically no more than two of H56, H57, and H58 in such compounds are substituted with deuterium (and often only one of the positions is filled by a deuterium atom). In other aspects, the invention provides pharmaceutical formulations comprising such compounds according to Formula I or Formula II as so modified and methods of using such compounds to modulate the physiology of mammalian hosts, such as in treating or preventing one or more conditions associated with such modulation (e.g., treatment of endometriosis-associated pain in a human female patient). The details of such aspects of the invention are provided elsewhere herein.

In a particular set of aspects, the invention provides compounds according to Formula I wherein all of R1, R2, R3, R4, R5, and R6 are deuterium atoms. Such a composition may comprise 7, 8, or 9 deuterium atoms. In one embodiment, the only deuterium atoms in the composition are the six found at positions R1, R2, R3, R4, R5, and R6. In other aspects, the invention provides pharmaceutical formulations comprising such compounds (according to Formula I and as modified by any of the variations thereof discussed above) and methods of using such compounds to modulate the physiology of mammalian hosts, such as in treating or preventing one or more conditions associated with such modulation (e.g., treatment of endometriosis-associated pain in a human female patient). The details of such aspects of the invention are provided elsewhere herein.

In another particular aspect, the invention provides compounds according to Formula X, which is shown here:

("Formula X" or "Formula 10")

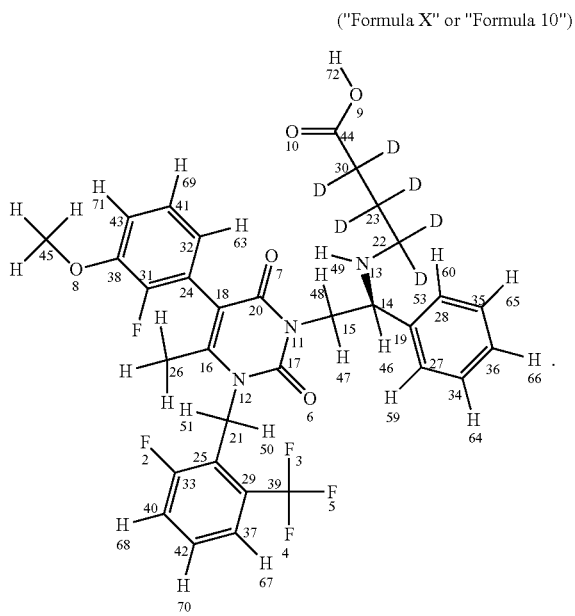 [SMILES: [2H]C([2H])(N[C@@H](Cn1c(=O)c(-c2cccc(OC)c2F)c(C)n(Cc2c(F)cccc2C(F)(F)F)c1=O)c1ccccc1)C([2H])([2H])C([2H])([2H])C(=O)O]

In other aspects, the invention provides pharmaceutical formulations comprising such compounds according to Formula X and methods of using such compounds to modulate the physiology of mammalian hosts, such as in treating or preventing one or more conditions associated with such modulation (e.g., treatment of endometriosis-associated pain in a human female patient). The details of such aspects of the invention are provided elsewhere herein.

The composition of compounds of the various general formulas (e.g., Formula I) and specific formulas (e.g., Formulas 17-36) presented above typically will able to be characterized as amorphous and/or hygroscopic, however the compound according to aspects may be in crystalline form and/or a composition of the invention can comprise compounds according to the formulas provided above in a mixture of crystal and amorphous forms. In many aspects, compounds provided herein will not spontaneously form (or convert to) polymorphs under typical storage conditions or in vivo following administration to a mammalian host, such as a human patient.

The above-described formulas can readily be used to develop specific compounds encompassed by the invention or encompassed by the inventive methods of the invention.

An example of a compound that can be incorporated into the compositions of the invention and/or employed in the methods of the invention is elagolix-d3, wherein H73, H74, and H75 are all substituted with deuterium, as reflected in the following structure:

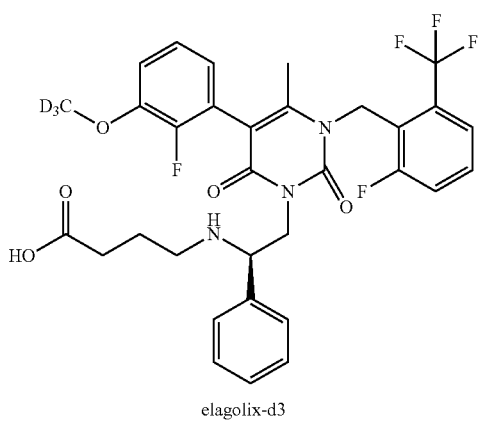 [SMILES: [2H]C([2H])([2H])Oc1cccc(-c2c(C)n(Cc3c(F)cccc3C(F)(F)F)c(=O)n(C[C@H](NCCCC(=O)O)c3ccccc3)c2=O)c1F]

elagolix-d3

The specific structure of elagolix-d3, as shown above, reflects a stereoisomer around the bond to the benzyl ring shown at the bottom of the figure (i.e., Ring B). In some embodiments there may also or alternatively be isomerization around the amino group shown near ring B, as reflected in, e.g., Formula I (above). Compounds of the invention (e.g., compounds according to Formula I or any of the formulas provided herein) can include either or both forms of isomerization around these and other indicated positions (e.g., either type of isomerization around the amino group and/or either type of isomerization around Ring B).

In a specific aspect of the invention, a mammalian subject, particularly a human patient, which can be either a male patient or a female patient, is administered elagolix-d3 or a similar compound (e.g., a deuterated elagolix analog in which two of H73, H74, and H75 are substituted with deuterium or one of H73, H74, and H75 are substituted with deuterium, which may be collectively referred to with elagolix-d3 as "methoxy side chain deuterated elagolix compounds"), typically in a pharmaceutically acceptable composition, and commonly as a salt of such a methoxy side chain deuterated elagolix compound (e.g., a sodium salt of elagolix-d3), so as to achieve any of the effects described herein with respect to elagolix and compositions of the invention (e.g., modulating gonadotropin-releasing hormone receptor (GnRHR) activity or to treat any of the various conditions associated with such compounds, such as treatment of endometriosis-associated pain in women). Typically, such a method will comprise repeatedly administering the methoxy side chain deuterated elagolix compound composition over a period of time that represents a course of treatment in accordance with a treatment regimen. According to embodiments, the amount of such a composition that is administered to the patient is markedly reduced over a period of time (e.g., per 12-hour period, per day, per every two days, per week, and/or per month, etc.) as compared to the amount of elagolix necessary to achieve a therapeutically similar result in a substantially similar treatment regimen (e.g., is at least about 10% less, is at least about 20% less, is at least about 30% less, is at least about 40% less, is at least about 50% less, is at least about 60% less, is at least about 70% less, or is at least about 80% less than the amount of elagolix needed to achieve a similar result). According to embodiments such methods can comprise effective treatment of endometriosis-associated pain, for example, by twice daily administration of about 20-180 mg (i.e., about 20 to about 180 mg), about 25-175 mg, about 25-125 mg, about 20-160 mg, about 20-140 mg, about 20-120 mg, about 30-180 mg or about 30-150 mg, about 30-120 mg, about 30-90 mg, about 25-175 mg, about 25-150 mg, about 25-100 mg, about 25-75 mg, about 40-160 mg, about 40-120 mg, about 40-100 mg, about 40-80 mg, or about 50-150 mg, 50-125 mg, or about 50-100 mg of the methoxy side chain deuterated compound (or corresponding salt compound). A composition comprising such a compound may add increase the amount administered to the subject by about 10%, about 20%, about 25%, about 50%, about 75%, about 100% (i.e., may double the amount administered to the subject), about 150%, about 200%, about 250%, about 300%, about 350%, about 400%, about 500%, or about 1000% (5× the amount of the compound active pharmaceutical ingredient) or a range defined by any of these amounts (e.g., about 50%-500%, about 100%-1000%, or about 75%-about 400%). Specific aspects relating to exemplary dosage forms/formulations comprising compounds of the invention are described elsewhere herein.

Another specific example of such a compound is an analog of elagolix in which the change is that all of R1, R2, R3, R4, R5, and R6 are substituted with deuterium, the structure of which compound (referred to herein as elagolix-d6) is shown below:

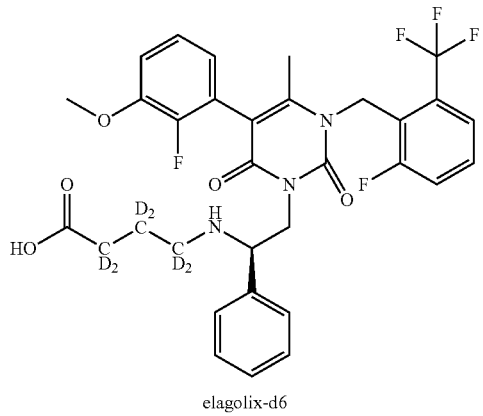

elagolix-d6

The specific form of elagolix-d6, as shown above, reflects the presence of isomerization around the bond to a benzyl ring (Ring B). As noted above, in some embodiments of the invention the compounds of the invention also or alternatively are characterized by isomerization around the amino group shown near Ring B (see, e.g., Formula I). As noted elsewhere, compounds of the invention can include either or both forms, i.e., isomerization around the amino group and/or isomerization around ring B.

It is expected the elagolix-d6 and similar compounds, such as compounds in which one, two, three, or four of R1-R6 are not deuterated, will be effective in the modulation of physiological effects in subjects or patients similar to elagolix, and may be used to treat the conditions described herein with respect to male and female human patients (e.g., treatment of endometriosis-associated pain). According to embodiments the amount of such a compound (e.g., elagolix-d6) or corresponding salt compound (e.g., elagolix-d6 sodium) administered to a patient over a period of time (e.g., every 12 hours, every day, every 2-days, every week, and/or every month) is at least about 5%, at least about 10%, at least about 15%, at least about 25%, at least about 35%, at least about 40%, or even at least about 50% reduced as compared to the amount of elagolix necessary to achieve a similar result in a similar administration/treatment regimen. According to embodiments, methods of treating conditions such as those described herein with elagolix d6 or such a similar compound as described in this paragraph comprise administering about 75-135 mg, about 75-125 mg, about 75-105 mg, about 80-140 mg or about 80-120 mg, about 90-140 mg, about 90-130 mg, about 90-120 mg, about 95-145 mg, about 95-135 mg, about 95-125 mg, or about 100-140 mg of elagolix-d6, a similar compound, or a salt of any thereof, typically once or twice a day.

In some aspects, the invention disclosed herein is a method of treatment comprising treating a target condition with any one or combination of compounds having any one or more of the formulas described herein. In some aspects, the target condition can be any target condition having been shown to be capable of improvement through administration of any one or more compounds having any one or combination of formulas described herein. Such conditions which may benefit from treatment using the compounds described herein are disclosed elsewhere within this disclosure, such conditions in some cases being capable of affecting female humans, male humans, male and female humans, or all mammals.

According to certain aspects, the invention described herein is a method of treating endometriosis-associated pain in a female mammal (e.g. a female human patient). According to certain aspects, the method comprises administration of a pharmaceutically acceptable composition comprising one or more compounds having a formula according to any of the formulas described herein. In certain aspects, the compound is a deuterated elagolix compound or an acceptable salt thereof comprising at least 1 deuterium atom. In certain embodiments, the compound in the composition as described comprises between 1 and 9 total deuterium atoms, such as for example 1 deuterium atom, 2 deuterium atoms, 3 deuterium atoms, 4 deuterium atoms, 5 deuterium atoms, 6 deuterium atoms, 7 deuterium atoms, 8 deuterium atoms, or 9 deuterium atoms. According to some embodiments, any one or more positions R1, R2, R3, R4, R5, and R6 (as previously described herein) of the compound are held by a deuterium atom. According to some embodiments, any one or more positions R1, R2, R3, R4, R5, and R6 of the compound are held by a hydrogen atom. In certain aspects, position R7 as previously described herein is held by a fluorine atom. In other aspects, position R7 is held by a chlorine atom. In certain further aspects, a deuterium atom is positioned at R1, R2, R3, R4, R5, or R6 or substitutes a hydrogen atom at position H73, H74, or H75. In some embodiments, the only locations within the compound wherein one or more deuterium molecules may be present are R1, R2, R3, R4, R5, or R6 or a deuterium can have substituted a hydrogen at H73, H74, and/or H75. In some aspects there are no other positions within the compound wherein a deuterium molecule is present. In some aspects, a compound of a composition used in a method to treat endometriosis-associated pain in a female human patient is present in an amount less than 150 mg, such as less than about 150 mg, less than about 140 mg, less than about 130 mg, less than about 120 mg, or less than about 110 mg, such as for example between about 10-120 mg, between about 20-120 mg, between about 30-120 mg, for example between about 40-120 mg, between about 60-110 mg, or between about 70-105 mg.

In certain aspects, the method of treating endometriosis-associated pain with a composition comprising one or more compounds described herein in an amount between about 40-120 mg comprises administering the composition at least once per day or at least twice per day. In certain aspects, the method of modulating GnRH receptor activity in a human subject, as described elsewhere herein, and/or other methods of treatment or physiological manipulation comprise administering about 40-120 mg of a compound (e.g. a compound that modulates GnRH receptor activity in humans) once per day. According to certain embodiments, treatment regimens comprising a compound of the present invention can comprise administration once per day ("daily") or twice per day ("twice daily") during at least a portion of a treatment period. A treatment period can be any period of time over which the compounds described herein are administered. For example, a treatment period may be about 1 month, about 2 months, about 3 months, about 4 months, about 5 months, about 6 months, about 7 months, or about 8 months or more, such as about 9 months, about 10 months, about 11 months, about 12 months or more, such as about 18 months or about 24 months or even more, such as for example at least 1 month, at least 3 months, at least 9 months, at least 12 months, at least 15 months, at least 18 months, at least 21 months, or at least 24 months. A portion of a treatment period could be any fraction of a treatment period, such as for example a one-month time span of time during a treatment period lasting at least one month (e.g. one month or longer). According to certain embodiments, the amount of compound administered, the frequency of the compound administration, or both the amount of compound administered and the frequency of the compound administration can vary during the course of a treatment period. In certain aspects, the frequency of the compound administration can increase over the course of a treatment period. In certain aspects, the frequency of the compound administration can decrease over the course of a treatment period. In certain aspects, the amount of compound administered can increase over the course of a treatment period. In certain aspects, the amount of compound administered can decrease over the course of a treatment period. In some aspects, the method of treating endometriosis-associated pain with a composition comprising one or more compounds described herein in an amount between about 40 mg and about 120 mg, such as for example between about 60 mg and about 110 mg or for example between about 70-105 mg comprises administering the composition once daily for at least a portion of, or at least some days of, a treatment period. According to certain embodiments.

More generally, compounds according to the invention can, according to embodiments, also or alternatively be characterized by having an in vivo half-life that is at least about 10%, at least about 15%, at least about 20%, at least about 25%, or at least about 33% increased over the in vivo half-life of a corresponding formulation/dose or amount of non-deuterated elagolix. In some embodiments, the invention provides compounds characterized in having an in vivo half-life of about 5-15 hours, more typically about 6-12 hours. In exemplary aspects the invention provides compounds that have an in vivo half-life of about 6 hours, about 7 hours, about 8 hours, about 9 hours, about 10 hours, about 11 hours, and/or about 12 hours. In some embodiments the invention provides compounds that have a half-life of at least about 7 hours, at least about 8 hours, or at least about 9 hours, commonly with a maximum half-life of about 10 hours, about 10.5 hours, about 11 hours, about 11.5 hours, or about 12 hours.

In one aspect, the invention as presently described provides compounds that experience slower metabolization by one or more human cytochrome P450 (CYP) enzymes than that experienced by elagolix, as reflected in suitable assays of such activity (see, e.g., Example 1, below). In some aspects, a deuterated compound as described herein is capable of maintaining an average percentage of parent compound remaining that is greater than twice that of elagolix, greater than about three times that of elagolix, greater than about 4 times that of elagolix, and in some cases almost five times that of elagolix, or more, or a range of such activity (e.g., about 100%-about 1000% increase in retained compound or corresponding effect, about 100%-500% increase in retained compound or corresponding effect, about 100%-400% increase in retained compound or corresponding effect, about 100%-300% increase in retained compound, about 200%-1000% in retained compound, or about 200%-500% increase in retained compound, as measured in a suitable measure or assay over a comparable period of time and conditions) (as exemplified in Example 1 described herein with elagolix-d6 and elagolix-d3). Elagolix-d3 and similar compounds (compounds with one, two, or three deuterium substitutions of H73, H74, and H75) can be, for example, capable of maintaining an average amount of parent compound in a cytochrome P450 (CYP) enzyme assay after 120 minutes that is more than about 400% that of elagolix. Elagolix-d6 and similar compounds (e.g., compounds with a number of modifications in R1-R6) can be capable of maintaining an average amount of parent compound in a CYP enzyme assay after 120 minutes that is more than about 100%, more than about 120%, or more than about 130% (e.g., 136%) that of elagolix.

The invention provides compositions that comprise, substantially comprise, substantially consist of, consist essentially of, or consist exclusively of a compound of the invention, the compound of the invention and one or more additional APIs that are useful in the treatment of a target disease or condition (e.g., endometriosis-associated pain, endometriosis, or uterine fibroids—including, e.g., elagolix), two or more isotopologues of a compound of the invention, and/or two or more compounds of the invention. Such compositions may be isolated or may be combined with devices or other chemicals (e.g., diluents, binders, carriers, and the like) to form a formulation. One aspect of the invention is pharmaceutical formulations comprising a therapeutically effective amount of a compound of the invention. As used herein, the term "effective amount" refers to an amount which, when administered in a proper dosing regimen, is sufficient to treat the target disorder and/or which has been demonstrated as being capable of treating the disorder in a signification proportion of a population in at least one well-controlled and adequate study and/or that is determined medically to be effective for treating a condition in a particular patient (e.g. through personalized medicine-related diagnostic methods). The phrase "well-controlled and adequate study" will be understood by those in the arts of pharmaceutical development and clinical practice as meaning a study that is sufficient in the given context to meet the requirements for supporting regulatory approval of a compound, such as adhered to in US regulatory affairs practice with respect to developing drugs for approval before US FDA.

In one exemplary aspect, compounds of the invention are formulated for oral administration. In one aspect, the compounds are formulated as capsules or tablets, and most typically tablets. According to specific embodiments the invention provides film coated, immediate release tablets comprising a therapeutically effective amount of a compound according to any of the formulas described above. In certain embodiments, the therapeutic effect may be dose-dependent. According to embodiments the compound, acting as the API for the pharmaceutical formulation, such as a tablet, will typically include one or more binders, diluents, or other functional excipients (such as antioxidants, preservatives, and the like) in combination with at least about 5 wt. %, at least about 10 wt. %, at least about 15 wt. %, at least about 20 wt. %, or at least about 25 wt. % of the compound or compounds of the invention to be contained therein. In certain aspects, the amount of compound included as API in a formulation, such as a tablet, will range from about 7 to about 42 wt. %, such as about 8 to about 40 wt. %, such as about 9 to about 36 wt. % (e.g., about 10-35 wt. % or about 10-40 wt. % or about 10-45 wt. % or about 15-35, -40, or -45 wt. % or about 20-30, -35, -40, or -45 wt. %). Typically, the amount of compound contained in, e.g., a single tablet for oral administration may be about 20-250 mg, such as about 30-250 mg or about 40-240 mg, e.g., about 45-225 mg, but more often will fall in the range of about 50-about 175 mg or about 50-about 135 mg or about 50-about 125 mg, and in particular aspects a tablet may include about 35-about 135 mg, about 65-about 165 mg, such as about 70-about 140 mg, e.g., about 75 mg to about 125 mg (e.g., about 60 mg, about 80 mg, about 100 mg, about 110 mg, about 120 mg, about 130 mg, about 150 mg, about 170 mg, or about 180 mg, or one or more values falling within a range of weights defined by any thereof, e.g., about 40-140 mg, about 30 mg-about 120 mg, about 60-about 110 mg, or about 80-about 120 mg). Commonly, a treatment regimen comprising administering a compound/composition of the invention will comprise administering such an amount of a compound, typically in an oral dosage form, such as in a tablet, once or twice a day, often twice a day, such that the daily dosage received in such a method is two times any of the amounts provided above (e.g., about 75 mg-about 275 mg/day or about 80 mg-about 280 mg/day such as about 120-about 280 mg/day, about 160-about 280 mg/day, about 100-about 280 mg/day or about 100-about 260 mg/day, about 140-about 280 mg day, or about 140-240 mg per day, about 140-220 mg per day, or about 150-210 mg/day or about 150-200 mg/day, such as about 150 mg/day, about 75 mg/day, about 100 mg/day, or about 200 mg/day).

According to specific embodiments, the total finished tablet weight, comprising API and all additional functional excipients, binders, diluents, carriers, coatings and elements which may comprise a finished product for delivery to a target patient, may range from about 100 mg to about 900 mg, more typically from about 200 mg to about 800 mg, for example about 300 mg to about 700 mg, about 400 mg to about 650 mg, or about 450 mg to about 650 mg, but in some aspects the total tablet weight may be, e.g., about 125-about 450 mg, such as about 150-about 400 mg, about 175 mg-about 375 mg or about 175 mg-about 350 mg, e.g., about 200-about 400 mg, about 250-about 400 mg, about 250-350 mg, or about 300-400 mg or about 350-450 mg. In another aspect, the amount of such excipients is reduced, in that the amount of active ingredient is also reduced due to the modified properties of the compound due to the particular effects of deuterization associated with the compound, such that the amount of excipient is about 10% less, about 20% less, about 25% less, about 30% less, about 40% less, or about 10-80% less, such as about 15-about 75% less than any of the above-referenced amounts.

Exemplary formulation elements that may be used to formulate a tablet according to the invention can include mannitol, sodium carbonate monohydrate, pregelatinized starch, povidone, magnesium stearate, polyvinyl alcohol, titanium dioxide, polyethylene glycol, and talc. According to embodiments the tablets can be packaged in standard packaging, such as blister packs, which may be substantially composed of foil and/or film materials. Typically, the formulation will be stable under typical conditions, such as storage from 2-30 degrees C. for at least about 12 months, more typically at least about 18 months or about 24 months.

Additional pharmaceutically acceptable carriers that may be incorporated into pharmaceutical formulations along with a compound, a number of isotopologues, derivatives, or a combination of compounds or a compound and one or more secondary agents, according aspects of the invention can include starches, pregelatinized starches, lactose, powdered celluloses, microcrystalline celluloses, dicalcium phosphate, tricalcium phosphate, mannitol, sorbitol, sugar, or the like; binders such as acacia, guar gum, tragacanth, gelatin, magnesium alumino-metasilicate), polyvinylpyrrolidones (PVPs) (e.g., polyvinylpyrrolidone K 30 (PVPK-30)), polyethylene glycol, copovidone, hydroxypropyl celluloses, hydroxypropyl methyl celluloses (HPMCs), or pregelatinized starches.

In some aspects the formulation can include one or more disintegrants such as starches, sodium starch glycolate, pregelatinized starches, crospovidones, croscarmellose sodium, colloidal silicon dioxide, or the like; lubricants such as stearic acid, magnesium stearate, zinc stearate, or the like; glidants such as colloidal silicon dioxide or the like; solubility or wetting enhancers such as anionic or cationic or neutral surfactants or the like; complex forming agents such as various grades of cyclodextrins or resins; release rate controlling agents such as hydroxypropyl celluloses (HPCs), hydroxymethyl celluloses, hydroxyethylcellulose, hydroxyethylmethylcellulose (HEMC), carboxymethylcellulose (CMC), carboxymethylhydroxyethylcellulose (CMHEC), hydroxyethylcarboxymethylcellulose (HECMC), sodium carboxymethylcellulose, cellulose acetate phthalate (CAP), hydroxypropyl methylcelluloses (HPMCs), hydroxypropylmethylcellulose acetate (HPMCA), hydroxypropylmethylcellulose phthalate (HPMCP), hydroxypropyl methyl cellulose acetate succinate (HPMCAS), Low-Substituted Hydroxypropyl Cellulose (HPC-L), ethylcelluloses, methylcelluloses, propylcellulose, hydroxyethyl methyl cellulose, hydroxyethyl cellulose acetate, hydroxyethyl ethyl cellulose, Syloid®, various grades of methyl methacrylates, poly(meth)acrylates (EUDRAGIT®), waxes, Soluplus® or the like. Other pharmaceutically acceptable excipients that may be incorporated according to embodiments include film formers, plasticizers, colorants, flavoring agents, sweeteners, viscosity enhancers, preservatives, antioxidants, or the like, examples of which are well known in the art.

A carrier contained in a formulation will typically be characterized as a "pharmaceutically acceptable carrier". Carrier(s) are "acceptable" in the sense of being compatible with the other ingredients of the formulation and, in the case of a pharmaceutically acceptable carrier, not deleterious to the recipient thereof in an amount used in the medicament. The same principle can be applied to characterize and limit diluents, binders, excipients in general, and any of the classes of excipients mentioned above, which can be used in formulations of the invention.

Additional pharmaceutically acceptable carriers, adjuvants, vehicles, and the like that also or alternatively may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, and polyethylene glycol.

The compound(s) of certain embodiments can be administered via any means demonstrated to be suitable for carrying out its intended use, such as, for example but not limited to, by injection, by mucosal absorption, or by oral ingestion. In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used in the formulation include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration can also include lozenges comprising the ingredients in a flavored base, usually sucrose and acacia or tragacanth; and pastilles comprising the active ingredient in an inert basis such as gelatin and glycerin, or sucrose and acacia.

In the pharmaceutical compositions of the invention, the compound of the present invention typically is present in a physiologically, a prophylactically, and most typically a therapeutically effective amount. Efficacious dosages of deuterated elagolix in the management of moderate to severe pain associated with endometriosis may be less than 200 mg, less than 150 mg, with a preferred range of approximately 100 mg or 75 mg, depending on the presence of coexisting conditions. Depending on the increase in terminal elimination half-life, a reduction in the dosing frequency for management of moderate to severe pain associated with endometriosis in the presence of coexisting conditions may be possible. As such, every-other-day administration of compounds of the invention, for example, may be possible with compounds of the invention, while retaining clinical efficacy. Dosages for other indications will have a similar relationship to dosages (amount and/or timing) that have been demonstrated to be effective for elagolix for the relevant indication and/or use or that in some cases can be modified from these amounts and/or timings of administration by the application of routine experimentation given this disclosure and knowledge in the art.

Compositions of the invention can be associated with detectably slower chemical reaction rates and/or detectably increased kinetic stability (KIE) as compared to non-deuterated elagolix (i.e., elagolix).

The invention also provides a variety of uses of the above-described compounds and formulations.

In one aspect, the invention provides a method for changing the physiology in a mammal, such as a human patient, comprising administering an amount of a compound of the invention, optionally in a formulation such as those described above, wherein the compound detectably competes with endogenous GnRH for GnRH receptor occupancy. According to embodiments, compounds of the invention bind the GnRH receptor without biologically stimulating the receptor. In a further embodiment of this aspect, the compound also can detectably suppress luteinizing hormone (LH), follicle-stimulating hormone (FSH), or both. In still another aspect, administration of a physiological effective amount of the compound to a mammal, such as a human patient, over a sufficient course of administration, leads to decreased blood concentrations of the ovarian sex hormones, e.g., estrogen(s) (e.g., estradiol) and progesterone.

In some aspects, the present invention describes a pharmaceutically acceptable formulation comprising any one or more of the compounds having a formulation described herein, wherein the compound is capable of causing a change to a physiological state, such as that which may occur via receptor modulation. The compounds of the present invention, and accordingly a composition or formulation in which they may be incorporated, can in some embodiments be capable of binding to a receptor so as to cause a physiological change in the recipient. Such a receptor can be any receptor to which the compound is capable of binding to a sufficient extent so as to cause a physiological change to, or modulation of, that receptor's activity. In certain aspects, the present invention is a pharmaceutically acceptable formulation comprising any one or more of the compounds having any one or more of the formulations described herein wherein the compound modulates GnRH receptor activity in human patients when present within a composition, formulation, or is otherwise administered in an amount less than about 150 mg. In some aspects, the GnRH receptor is in a human male patient. In certain alternative aspects, the GnRH receptor is in a human female patient.

According to certain aspects, the invention described herein is a formulation comprising any one or more of the compounds having any one or more of the formulas disclosed herein for modulating GnRH receptor activity to any given extent using an amount of compound that is at least 5% less, such as for example at least 10% less, at least 15% less, at least 20% less, at least 30% less, at least 35% less, at least 40% less, at least 45% less, or even at least 50% less than that required to obtain the same extent of GnRH receptor modulation using an otherwise equivalent formulation comprising elagolix in place of a compound disclosed herein. In certain aspects, the amount of compound present in such a formulation is less than approximately 150 mg, such as for example less than approximately 140 mg, less than approximately 130 mg, or less than approximately 120 mg, such as for example between about 10 mg and 150 mg, between about 20 mg and 150 mg, between about 30 mg and 150 mg, or for example between about 40 mg and 150 mg, such as for example between about 40 mg and about 140 mg, between about 40 mg and about 130 mg, or between for example about 40 mg and 120 mg.

In certain aspects, the formulation capable of modulating GnRH receptor activity to a beneficial extent using a lower concentration of compound that that which would be required by the use of elagolix comprises a compound having a formula wherein the compound is a deuterated elagolix compound or an acceptable salt thereof comprising at least 1 deuterium atom. In certain embodiments, the compound in the composition as described comprises between 1 and 9 total deuterium atoms, such as for example 1 deuterium atom, 2 deuterium atoms, 3 deuterium atoms, 4 deuterium atoms, 5 deuterium atoms, 6 deuterium atoms, 7 deuterium atoms, 8 deuterium atoms, or 9 deuterium atoms. According to some embodiments, any one or more positions R1, R2, R3, R4, R5, and R6 (as previously described herein) of the compound are held by a deuterium atom. According to some embodiments, any one or more positions R1, R2, R3, R4, R5, and R6 of the compound are held by a hydrogen atom. In certain aspects, position R7 as previously described herein is held by a fluorine atom. In other aspects, position R7 is held by a chlorine atom. In certain further aspects, a deuterium atom is positioned at R1, R2, R3, R4, R5, or R6 or substitutes a hydrogen atom at position H73, H74, or H75. In some embodiments, the only locations within the compound wherein one or more deuterium molecules may be present are R1, R2, R3, R4, R5, or R6 or a deuterium can have substituted a hydrogen at H73, H74, and/or H75. In some aspects there are no other positions within the compound wherein a deuterium molecule is present.

According to embodiments, compounds of the invention also or alternatively act as inducers, typically relatively weak to moderate inducers, of cytochrome (CYP) P450 3A. In still other embodiments compounds of the invention also or alternatively are metabolized by CYP3A and/or at least one other CYP450 enzyme. In other embodiments, compounds of the invention also or alternatively are inhibitors of efflux transporter p-glycoprotein (P-gp). In yet further embodiments, administration of a physiologically effective amount of compounds of the invention result in detectable binding between the compounds and OATP1B1. According to embodiments, in medical application of compounds and compositions of the invention, often a patient or health care provider is advised to limit or restrict the use of CYP3A inhibitors (or at least of strong CYP3A inhibitors) (e.g., to a period of time—such as a period of about six months or less) and/or to limit or exclude co-administration with drugs that may induce CYP3A (as such drugs may impair the efficacy of the compounds of the invention), and to limit or exclude concomitant use of organic anion transporting polypeptide (OATP) 1B1 inhibitors, especially strong OATP 1B1 inhibitors (e.g., cyclosporine and gemfibrozil).

According to embodiments, the compound is formulated for single dose daily oral administration and comprises about 25-about 100 mg of a compound of the invention and the AUC of the compound in one or more well-controlled and adequate clinical studies conducted with the formulation used in the method (comparable to the studies used to report AUC for elagolix, as reflected on its US FDA label) is at least about 1500 ng*h/mL (e.g., at least about 1600 ng*h/mL, such as at least about 1700 ng*h/mL, at least about 1800 ng*h/mL, or at least about 2000 ng*h/mL (e.g., about 1400-2400 ng*h/mL, about 1500-2250 ng*h/mL, about 1600-2200 ng*h/mL, about 1650-2150 ng*h/mL, about 1700-2100 ng*h/mL, about 1750-2050 ng*h/mL, or about 1800-2050 ng*h/mL.

According to other embodiments, the amount of the compound in each of the two daily administrations is about 50 mg to about 125 mg. With respect to such embodiments, the mean AUC measured in at least one well-controlled and adequate study achieved by performance of the method with the twice daily administration of the compound may be at least about 1850 ng*h/mL, such as at least about 1900 ng*h/mL, and typically will be at least about 2000 ng*h/mL (e.g., at least about 2200 ng*h/mL, or at least about 2350 ng*h/mL). In some embodiments, the mean AUC by performance of such a twice-a-day administration regimen will be at least about 2500 ng*h/mL (e.g., at least about 2650 ng*h/mL), such as at least about 2750 ng*h/mL (e.g., about 1900-about 2900 ng*h/mL, such as about 2000-about 2800 ng*h/mL, e.g., about 2150-about 2850 ng*h/mL, e.g., about 2250-2750 ng*h/mL).

According to either once daily, twice daily, or an alternative dosing strategy using compounds (or formulations) of the invention, the method can in some embodiments be characterized in that the accumulation of the compound in vivo is at least about 20% greater (e.g., at least about 25% or more or at least about 33% or more) than the accumulation of the same amount of elagolix in a similarly timed dosing regimen. According to embodiments, the methods of the invention also or alternatively can be characterized in that the in vivo clearance (e.g., the apparent oral clearance) associated with the compound is at least about 20% lower than the clearance of the counterpart administration strategy of the same amount or corresponding amount of elagolix (e.g., the clearance rate, such as the apparent oral clearance rate, is at least about 25% lower, at least about 30% lower, at least about 33% lower, or even at least about 40% or at least about 50% lower than a corresponding apparent oral clearance or other clearance rate for a corresponding dosing strategy and/or amount of elagolix).

Compounds of the invention when applied in the above-described once or twice daily dosing strategies also or alternatively can be characterized further by having a Cmax that occurs about 1 hour, about 75 minutes, about 80 minutes, about 90 minutes, or about 120 minutes after dosing. Cmax values achieved by the performance of such methods may range from about 500 to about 1000 ng/mL, such as about 550-950 ng/mL, e.g., about 575-875 ng/mL.

The compounds and compositions of the invention can be used in therapeutic methods for the treatment of a variety of disorders and diseases, such as the treatment of disorders associated with uterine fibroids and/or the treatment of endometriosis-associated pain.

In one embodiment, the patient is a female suffering from endometriosis and/or experiencing endometriosis-associated pain, typically moderate to severe endometriosis pain, and the method detectably treats the pain or the method has been demonstrated to treat endometriosis-associated pain (e.g., moderate to severe endometriosis-associated pain) in at least one well-controlled and adequate clinical study. For each method of treatment provided herein, methods of prevention (prophylaxis) also are provided. Thus, for example, a method of preventing endometriosis pain is provided comprising administering a prophylactically effective amount of a compound of the invention to a patient so as to reduce the likelihood of occurrence of endometriosis pain, reduce the severity of subsequently developing endometriosis pain, reduce the area of endometriosis-associated pain, and/or to reduce the duration of subsequently developed endometriosis pain in the patient, and typically such effect of the method will have also or alternatively first been demonstrated to be prophylactically effective against the relevant disease or condition through at least one well-controlled and adequate clinical study.

In another embodiment, the patient is a female diagnosed as also or alternatively suffering from a condition associated with uterine fibroids and the performance of the method detectably treats the woman or is associated with the treatment of a significant proportion of women having the condition or a medically similar condition in a well-controlled and adequate clinical study.

In another aspect of the invention, the compounds of the invention and/or the methods of the invention are applied as or in the context of applying assisted reproductive technology ("ART") to treat infertility, typically by detectably increasing the chance of successful initiation of pregnancy and/or live birth of a child in pregnant women (e.g., as determined by clinical experience and/or through well-controlled and adequate clinical studies). ART typically involves in vitro fertilization (IVF). According to embodiments, the performance of the methods described herein (relating to administration of the compounds and/or compositions of the invention) detectably reduces the chance of cycle cancellation in a patient or in a significant amount (proportion) of patients, such as a proportion of patients in a well-controlled and adequate study of such a condition.

According to embodiments, methods of the invention are used to control, optimize, or regulate the amount of estradiol in a patient. In certain embodiments, application of the methods provided herein may even result in increases in estradiol or other estrogen amounts in subjects, and such results may assist in, e.g., ART, or in the treatment and/or prevention of other conditions.

According to embodiments, the practice of the methods provided herein also or alternatively detectably reduces the likelihood, amount, duration, etc., of a luteinizing hormone (LH) increase (or "surge") in a patient or in such a proportion of patients, such as patients receiving ART. Thus, for example, the incidence and/or magnitude of such an LH surge may be reduced by at least about 5%, at least about 10%, at least about 15%, at least about 20%, at least about 30%, or more, or by some other statistically significant amount, as determined by clinical observation and/or relevant well-controlled and adequate clinical studies in animal models, human patients, or both.

In still further embodiments, the methods and/or compounds of the invention also or alternatively detectably modulate the activity of the hypothalamic-pituitary-adrenal (HPA) axis and/or the hypothalamic-adrenal-gonadal (HPG) axis.

In certain embodiments, the methods and/or compounds of the invention as described herein also or alternatively detectably reduce the level of negative side effects which may be experienced by target subjects below that which may be experienced by target subjects having been given a dose of elagolix capable of achieving an equivalent level of clinical result. That is, according to certain embodiments, a dose of elagolix required to achieve a target clinical result can be higher than that required of any one or more of the compounds having any one or more of the formulas described herein, hence a lower dose of a compound of the present invention can be expected to be necessary to achieve an equivalent clinical results. Having been given a lower required dose, it can be expected that users administered a compound of the present invention in place of elagolix may experience a lower level of side effects from treatment than those having received elagolix. Side effects reported by elagolix users as noted in the art include but may not be limited to decreased hepatic function or hepatic health (hepatic impairment), decreased renal function or renal health (renal impairment), bone loss (e.g., decrease in bone mineral density), hot flushes, night sweats, headache, nausea, insomnia, amenorrhea, anxiety, arthralgia, depression, mood changes, changes in menstrual bleeding patterns, reduced ability to recognize pregnancy, A reduction in such side effects can be as measured in and reported by an appropriately conducted clinical trial or an appropriately powered consumer survey. Such studies can be expected to result in demonstration of side effects (e.g., as measured by pain scores, blood markers, disease risk factors, organ function markers and the like) which are at least 1%, at least 3%, at least 5%, at least 10%, at least 15%, at least 20%, at least 30%, at least 35%, at least 40%, at least 45%, or even at least 50% less frequent in populations administered a compound of the present invention than those in populations administered elagolix for equivalent indications. Also or alternatively it can be expected that such studies would demonstrate that side effects are at least 1%, at least 3%, at least 5%, at least 10%, at least 15%, at least 20%, at least 30%, at least 35%, at least 40%, at least 45%, or even at least 50% less severe in populations of subjects administered a compound of the present invention than those in populations administered elagolix for equivalent indications.

Methods and principles relevant to the preceding several and following several paragraphs with respect to the use of elagolix are provided in Struthers et al., J Clin Endocrinol Metab. 2009 February; 94(2): 545-551 and Ng et al., J Clin Endocrinol Metab. 2017 May 1; 102(5):1683-1691. Additional disclosures relating to elagolix and other GnRH antagonists useful in the preceding and following methods include those found in US Patent Publication 20150335701 and International Patent Application WO2018060438. It is expected that while the timing of dosing may be similar (once-per-day, twice daily, etc.) as in methods known with respect to elagolix, the effective dosage of compounds of the invention will typically be equal, and often less, e.g., at least about 10% less, at least about 15% less, at least about 20% less, at least about 30% less, at least about 40% less, or at least about 50% lower than that used in the corresponding elagolix method (e.g., about 5%-about 75% less, such as about 7.5%-about 67.5% less, such as about 10% to about 60% less, such as about 12.5% to about 50% less). This principle of a relatively lower effective dose associated with compounds, compositions, and methods of the invention as compared to corresponding methods involving elagolix is generally applicable throughout the various methods of treatment and modulating physiochemical activity in subjects described herein.

In still other exemplary embodiments, the methods, compounds, and/or compositions of the invention detectably and typically significantly regulate oocyte maturation, ovulation, and/or steroid hormone production in tissues, typically in women in vivo, such as pregnant patients (either in a specific patient or a significant proportion of patients as determined through clinical experience, in vitro tests, and/or one or more well-controlled and adequate clinical studies). According to exemplary embodiments, administration of compounds or compositions of the invention results in a dose-dependent suppression of luteinizing hormone (LH) and/or follicle-stimulating hormone (FSH), leading to decreased blood concentrations of the ovarian sex hormones, estradiol and progesterone. Similar aspects of the invention are described elsewhere herein.

According to embodiments, the compounds and compositions of the invention also or alternatively detectably reduce gonadotrophin secretion in mammals, such as human females (e.g., as determined by clinical study). The degree of modulation of this and other physical processes by administration of the compounds or compositions of the invention will depend on the amount and type of compound or composition administered, as most of the compounds of the invention are non-activating competitive antagonists of receptors/ligands, such as the GnRH receptor.

According to embodiments a patient treated by administration of the method, such as a patient being treated for endometriosis and/or endometriosis-associated pain, is a human female diagnosed as suffering from dysmenorrhea (menstrual cramps), often in association with another disease or condition, such as endometriosis, or endometriosis-associated pain, and the method comprises detectably treating the dysmenorrhea in the patient or the method has been demonstrated to treat dysmenorrhea in at least one well-controlled and adequate clinical study. In another aspect, the method is performed in a female diagnosed as suffering from non-menstrual pelvic pain (NMPP) and the method comprises detectably treating the NMPP in the patient or the method has been demonstrated to treat NMPP in at least one well-controlled and adequate clinical study.

In still further embodiments, the patient treated by a method of the invention is a female and the method is associated with a statistically significant reduction in hot flashes, night sweats, or both in patients in at least one well-controlled and adequate clinical study of the patients, either against placebo or as compared to clinical data (prior or concurrently obtained) associated with elagolix. Such patients may be patients suffering from, e.g., endometriosis-associated pain, or one of the other indications descried herein wherein such effects are beneficial.

The above-described therapeutic methods, such as the methods relating to the treatment of endometriosis pain, are typically performed for a period of up to about six months, but in some cases the course of treatment can be extended to about 12 months, about 18 months, or even about 24 months, such as where the patient has no coexisting conditions or conditions that may dictate more limited use of the therapeutic method. Similarly, the amount of compound administered in the method, and whether the compound is administered twice-per-day, once-per-day, or by and alternative dosing strategy, will depend on the relevant condition. In one aspect, the therapeutic method application corresponds to the differential dosing strategies of elagolix (i.e., having a set of relatively higher and lower dosing frequency and amount depending on the condition to be treated), e.g., with higher dosing (e.g., about 100-175 mg of a compound of the invention) and more frequent dosing (2x/day) for a shorter duration (about 6 months or less) in women undergoing both endometriosis-associated pain and dyspareunia, with lower dosing (e.g., about 25-100 mg), less frequently (e.g., once per day), for a longer duration (e.g., up to 12, 18, or about 24 months) with women with only medium to severe endometriosis pain without other conditions.

In some embodiments, the patient is a male that has been diagnosed with prostate cancer or benign prostatic hyperplasia (enlarged prostate) and the method comprises treating the prostate cancer, benign prostatic hyperplasia, or both in the male patient or the method has been demonstrated to treat prostate cancer, benign prostatic hyperplasia, or both in at least one well-controlled and adequate clinical study.

In some embodiments the method is effective in at least about 20%, at least about 25%, at least about 30%, or at least about 35% more of patients treated with a compound of the invention than placebo, elagolix, or both. According to embodiments, at least 40% of patients treated in at least one well-controlled and adequate study, typically at least about 45%, at least about 50%, at least about 55%, at least about 60%, at least about 65%, or even at least about 70% of patients receiving the method are effectively treated or at least exhibit a statistically significant improvement in one or more symptoms, markers, or indicators of the disease or condition.

Measurements of efficacy for these conditions are known in the art and have been applied with respect to elagolix treatment and development. For example, a Daily Endometriosis Pain Impact Scale has been used by Abbvie in connection with the development of elagolix, which can similarly be used to diagnose conditions in the context of the inventive methods provided herein, and to also judge the efficacy of treatment. Relevant references in this respect include the ORILISSA [package insert]. North Chicago, Ill.: AbbVie Inc. and Taylor H S, Giudice L C, Lessey B A, et al. Treatment of endometriosis-associated pain with elagolix, an oral GnRH antagonist. *N Engl J Med.* 2017; 377(1):28-40. An example of a scale used by Abbvie in connection with elagolix is shown below:

| DYSNMENORRHEA AND NMPP | | DYSPAREUNIA | |
|---|---|---|---|
| 3 Severe | Severe pain. I had great difficulty doing the things I usually do. | 3 Severe | I avoided sexual intercourse because of pain. |
| 2 Moderate | Moderate discomfort or pain. I had some difficulty doing the things I usually do. | 2 Moderate | Intercourse was interrupted due to pain. |
| 1 Mild | Mild discomfort but I was easily able to do the things I usually do. | 1 Mild | I was able to tolerate the discomfort during sexual intercourse. |
| 0 None | No discomfort. | 0 None | No discomfort during sexual intercourse. |

According to embodiments, performance of the method will result in a decrease of at least about 1 point in a statistically significant number of patients (as determined by at least one well-controlled and adequate study), and in some embodiments the average decrease is at least about 1.25, at least about 1.5, at least about 1.75, at least about 2, at least about 2.25, or even at least about 2.5 in the pain score in the above-referenced scales or a substantially similar scale. According to embodiments the decrease in pain on the pain scale also or alternatively is reflected in at least an about 0.5, at least an about 0.75, at least an about 1, or at least an about 1.25 decrease greater than placebo (on average). The decrease may increase in patients treated with higher dosing and/or greater frequency dosing of the compounds of the invention.

In certain aspects, the performance of the method is associated with a significantly lower incidence of headache, a significantly lower incidence of nausea, a significantly lower incidence and/or lower severity of bone mineral density loss, and/or a significantly lower incidence of appendicitis, abdominal pain, and/or back pain than is observed with a corresponding dosing frequency and/or amount of elagolix. In still other embodiments, the elevation of serum ALT (liver enzyme) associated with performance of the method is at least 25% less than, at least 33% less than, at least about 40% less than, or at least about 50% less than the corresponding level observed with the counterpart dosing frequency and/or amount of elagolix. In still another embodiment, the frequency and/or severity of mood swings, depression, or both, in subjects receiving the method of the invention is at least about 25% less than, at least 33% less than, at least about 40% less than, or at least about 50% less than the corresponding frequency and/or severity level observed with the counterpart dosing frequency and/or amount of elagolix.

In yet another aspect, a method of the invention as described above is performed with a compound exhibiting an increase in the terminal elimination half-life and a dose that is at least 15%, at least 22.5%, at least 30%, at least 37.5%, or at least 45% reduced compared to a corresponding dose of elagolix in the context of the dosing regimen and condition at issue, resulting in a reduction of adverse side-effects such as the likelihood of liver injury arising from administration of the compound, as compared to elagolix, due to elevated hepatic transaminase levels.

The compounds, compositions, and methods of the invention also or alternatively can be used to treat and/or prevent one or more conditions selected from polycystic ovarian disease, hirsutism, precocious puberty, sleep apnea, irritable bowel syndrome, and premenstrual syndrome, and may also or alternatively be useful in procedures relating to contraception and infertility (e.g., assisted reproductive therapy such as in vitro fertilization).

Compounds, compositions, and methods of the invention also or alternatively can be used to treat and/or prevent benign prostatic hypertrophy, gonadal steroid-dependent neoplasia such as cancers of the prostate, breast and ovary, and gonadotrophic pituitary adenomas.

The compounds of this invention are also or alternatively useful as an adjunct to treatment of growth hormone deficiency and short stature, and for the treatment of systemic lupus erythematosus.

Compounds 1-4 and the other two compounds disclosed in the '400 application, and any derivative of any one or more of such compounds also or alternatively can be used in the above-described methods and can be incorporated into the formulations described herein. Given the limited disclosure in the '400 application the use of compound 1, compound 2, compound 3, compound 4, and/or the other two compounds explicitly disclosed in the '400 application, and/or any derivative of any one or more of such compounds, in such methods and incorporation of such compounds into the formulations of this invention in the indicated amounts with the indicated excipients, etc., in and of itself, is expected to be inventive.

As indicated above, the compounds of the invention can be combined with each other or combined with other agents in the treatment or prevention of diseases or conditions, including any one of the six compounds disclosed in the '400 application, their derivatives, and/or elagolix and/or any of the elagolix derivatives, analogs, and formulations described in the art, including in the references incorporated by reference herein.

For example, compounds of the invention can be useful in combination with, e.g., estrogens (e.g., estradiol and estradiol analogs, derivatives, etc.), progesterone (and progesterone analogs, derivatives, etc.), and antiestrogens and antiprogestogens for the treatment of endometriosis, fibroids, and in contraception, as well as in combination with an angiotensin-converting enzyme inhibitor, an angiotensin II-receptor antagonist, or a renin inhibitor for the treatment of uterine fibroids. In addition, the compounds may be used in combination with bisphosphonates and other agents for the treatment and/or prevention of disturbances of calcium, phosphate and bone metabolism, and in combination with estrogens (e.g., estradiol or an estradiol derivative and/or analog), progesterones and/or androgens for the prevention or treatment of bone loss or hypogonadal symptoms such as hot flashes during therapy with a GnRH antagonist.

According to certain aspects, the methods of the invention are performed in the absence of an intake of a high fat meal. According to certain aspects, the methods of the invention are performed in the presence of an intake of a high fat meal.

Methods of producing deuterated compounds that can be applied to the production of the compounds disclosed herein are known in the art. Such methods generally include "hydrogen-deuterium exchange" or "H-D exchange" or "H/D exchange": a chemical reaction where covalently bonded hydrogen atom is replaced by a deuterium atom, or vice versa. The use of acid, base or metal catalysts, coupled with conditions of increased temperature and pressure, can facilitate the exchange of non-exchangeable hydrogen atoms.

EXAMPLES

Example 1: Effect of Deuteration on Elagolix Metabolism by Human Cytochrome P450 Isoforms A study was conducted to determine the effect of deuteration on the metabolism of elagolix by human cytochrome P450 (CYP) enzymes. The metabolism of 4-[[(1R)-2-[5-(2-fluoro-3-methoxyphenyl)-3-[[2-fluoro-6 (trifluoromethyl)phenyl]methyl]-3,6-dihydro-4-methyl-2,6-dioxo-1(2H)-pyrimidinyl]-1-phenylethyl]amino] butanoic acid-d3 (elagolix-d3) sodium salt and 4-[[(1R)-2-[5-(2-fluoro-3-methoxyphenyl)-3-[[2-fluoro-6(trifluoromethyl) phenyl] methyl]-3,6-dihydro-4-methyl-2,6-dioxo-1(2H)-pyrimidinyl]-1-phenylethyl]amino] butanoic acid-d6 (elagolix-d6) sodium salt by cDNA-expressed CYP enzymes were investigated in vitro and compared to results obtained with undeuterated elagolix to determine which human cytochrome P450 (CYP) enzymes are involved in the metabolism of elagolix, elagolix-d3, and elagolix-d6.

Commercially available cDNA-expressed human CYP enzymes were used for this study.

A 600 μL reaction mixture containing enzyme protein, NADPH generating system (1.3 mM NADP+, 3.3 mM glucose-6-phosphate, 0.4 U/mL glucose-6-phosphate dehydrogenase, 3.3 mM magnesium chloride) and each test article (elagolix, elagolix-d3, elagolix-d6) at two concentrations (e.g. 1 μM and 10 μM) in 100 mM potassium phosphate (pH 7.4) was incubated at 37° C. At two time points (0 and 120 min), the reaction was stopped by removing an aliquot and combining it with an equal volume of cold acetonitrile containing an internal standard (deuterated elagolix was used as the internal standard for elagolix, and elagolix was used as the internal standard for elagolix-d3 and -d6) and placed on ice. Samples were centrifuged to pellet the protein and the supernatant was frozen at −20° C. for subsequent analysis by LC-MS/MS.

Protein concentrations were constant for all isoforms within each experiment and standardized by the addition of control microsomes. Incubations were performed in duplicate. Incubations with vector control enzyme preparations and without enzyme source were included as negative controls.

For the positive control coumarin (CYP2A6), a 400 μL reaction mixture containing enzyme protein, NADPH generating system (1.3 mM NADP+, 3.3 mM glucose-6-phosphate, 0.4 U/mL glucose-6-phosphate dehydrogenase, 3.3 mM magnesium chloride) and one concentration of substrate in 100 mM potassium phosphate (pH 7.4) was incubated at 37° C. for 20 minutes (CYP2A6). The reaction was stopped by adding 100 μL of cold acetonitrile containing an internal standard (labetalol). The formation of 7-hydroxy coumarin was quantified based on a standard curve.

All other positive controls were assayed at one concentration in duplicate in accordance with the methods described above. The percent of parent remaining at the end of the incubation was compared to 0 min based on the peak area ratio of the substrate and internal standard.

LC-MS/MS methods for elagolix, elagolix-d3, and elagolix-d6 were developed. The fraction of parent compound remaining compared to 0 min was determined based on peak area ratio (analyte/internal standard).

Elagolix, elagolix-d3, and elagolix-d6 at 1.0 μM and 10 μM were each incubated in the presence of cDNA-expressed CYP1A2, CYP2A6, CYP2B6, CYP2C8, CYP2C9, CYP2C19, CYP2D6, CYP2E1, CYP3A4, and CYP3A5 for 120 minutes. The average percent of parent compound remaining for all isoforms and concentrations was >11% for elagolix, >60% for elagolix-d3, and >26% for elagolix-d6.

In particular, undeuterated elagolix at 1 μM showed significant loss when metabolized by cDNA-expressed CYP2D6 and CYP3A5, with 62% and 11% remaining, respectively. Unexpectedly, elagolix-d3 did not demonstrate any depletion by cDNA-expressed CYP2D6 and showed 60% remaining by cDNA-expressed CYP3A5 at this condition. The results of these studies indicate that deuteration of the elagolix methoxy side-chain has a significant kinetic isotope effect on elagolix metabolism by cDNA-expressed CYP2D6 and CYP3A5.

EXEMPLARY ASPECTS OF THE INVENTION

The following is a non-limiting list of exemplary aspects of the invention, which is intended to highlight some of the various embodiments of the invention. Any one or more aspects of the following list, as with any one or more embodiments or aspects described within this disclosure, should be interpreted as being capable of being combined with any other one or more embodiments or aspects or combination of embodiments or aspects, as is also the case with respect to the various aspects and embodiments described above (except where explicitly otherwise stated or clearly contradicted).

1. A compound having a structure according to Formula I

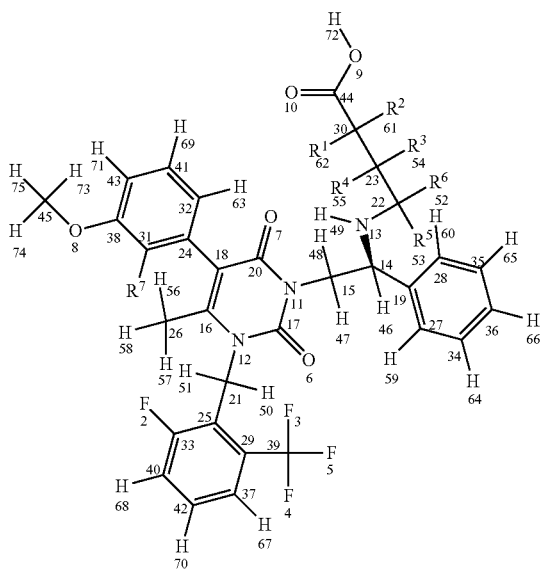

or a pharmaceutically acceptable salt thereof, wherein (a) R1, R2, R3, R4, R5, and R6 are either deuterium or hydrogen; (b) at least one of R1, R2, R3, R4, R5, or R6, is deuterium or deuterium substitutes a hydrogen at position H56, H57, H58, H73, H74, or H75; (b) R7 is either fluorine or chlorine; and (c) the compound comprises between 1-9 deuterium atoms, wherein 0-8 of the hydrogen atoms in Formula I are substituted with deuterium.
2. The compound of aspect 1, wherein R7 is fluorine.
3. The compound of aspect 1 or aspect 2, wherein at least 75% of the 1-9 deuterium atoms in the compound are located at positions R1, R2, R3, R4, R5, or R6 or substitute a hydrogen at position H56, H57, H58, H73, H74, or H75.
4. The compound of aspect 3, wherein all of the 1-9 deuterium atoms in the compound are located at positions R1, R2, R3, R4, R5, or R6 or substitute a hydrogen at position H56, H57, H58, H73, H74, or H75.
5. The compound of aspect 4, wherein at least 75% of the 1-9 deuterium atoms are located at positions R1, R2, R3, R4, R5, or R6 or substitute a hydrogen at position H56, H57, or H58.
6. The compound of aspect 5, wherein the hydrogens at positions H73, H74, and H75 are maintained.
7. The compound of aspect 6, wherein all of the 1-9 deuterium atoms are located at positions R1, R2, R3, R4, R5, or R6 or substitute a hydrogen at position H56, H57, or H58.
8. The compound of aspect 7, wherein the compound comprises at least two deuterium atoms.
9. The compound of aspect 8, wherein the compound comprises at least four deuterium atoms, wherein at least one of the deuterium atoms substitute a hydrogen at position H56, H57, or H58.
10. The compound of aspect 9, wherein at least 2 of R1, R2, R3, R4, R5, and R6 are deuterium.
11. The compound of aspect 10, wherein at least 3 of R1, R2, R3, R4, R5, and R6 are deuterium.
12. The compound of aspect 11, wherein no more than two deuterium atoms substitute hydrogens at positions H56, H57, and H58.
13. The compound of any one of aspects 1-12, wherein the compound comprises no more than five deuterium atoms.
14. The compound of any one of aspects 1-12, wherein the compound contains 6-9 deuterium atoms.
15. The compound of aspect 14, wherein at least 4 of R1, R2, R3, R4, R5, and R6 are deuterium.
16. The compounds of aspect 15, wherein at least 5 of R1, R2, R3, R4, R5, and R6 are deuterium.
17. The compound of aspect 16, wherein all of R1, R2, R3, R4, R5, and R6 are deuterium.
18. The compound of aspect 17, wherein the compound contains 6-8 deuterium atoms.
19. The compound of aspect 18, wherein the compound contains 6-7 deuterium atoms.
20. The compound of aspect 19, wherein the compound contains 6 deuterium atoms.
21. A compound comprising a salt form of any one of the compounds of aspects 1-20.
22. The compound of aspect 21, wherein the compound is a sodium salt of a compound according to any one of aspects 1-20.
23. The compound of any one of aspects 1-22, wherein the compound has a half-life of about 6-about 12 hours in a human subject.
24. The compound of aspect 23, wherein the compound has a half-life of at least about 7 hours.
25. The compound of aspect 24, wherein the compound has an in vivo half-life of at least about 8 hours.
26. A composition comprising at least 1 mcg of a mixture of at least two isotopologues, wherein at least one of the at least two isotopologues is a compound according to any one of aspects 1-25.
27. The composition of aspect 26, wherein the average deuteration rate is at least about 75% in all positions in which a hydrogen is replaced by a deuterium.
28. The composition of aspect 27, wherein the average deuteration rate is at least about 95%.
29. The composition of aspect 28, wherein the average deuteration rate is at least 99%.
30. The composition of aspect 29, wherein the average deuteration rate is at least 99.5%.
31. A pharmaceutically acceptable formulation comprising a therapeutically effective amount of a compound according to any one of aspects 1-25 or a composition according to any one of aspects 26-29 and at least one pharmaceutically acceptable carrier, diluent, or excipient.
32. The formulation of aspect 31, wherein the formulation comprises about 25-250 mg of the compound or composition.
33. The formulation of aspect 32, wherein the formulation comprises about 35 mg to about 200 mg of the compound or composition.
34. The formulation of aspect 33, wherein the formulation comprises about 40 mg to about 150 mg of the compound or composition.
35. The formulation of aspect 34, wherein the formulation comprises about 50 mg to about 135 mg of the compound or composition.
36. The formulation of aspect 35, wherein the formulation comprises about 65 mg to about 130 mg of the compound or composition.

37. The formulation of aspect 36, wherein the formulation comprises about 75 mg, about 100 mg, or about 125 mg of the compound or composition.
38. The formulation of any one of aspects 31-37, wherein the formulation is in the form of a tablet for oral administration.
39. The formulation of aspect 38, wherein the formulation is stable at 2° C. to 30° C. for at least 24 months.
40. The formulation of aspect 39, wherein the formulation comprises three or more excipients selected from the group consisting of mannitol, sodium carbonate monohydrate, pregelatinized starch, povidone, magnesium stearate, polyvinyl alcohol, titanium dioxide, polyethylene glycol, and talc.
41. A method of modulating GnRH receptor activity comprising administering to a mammalian subject a physiologically effective amount of a compound according to any one of aspects 1-25, a composition according to any one of aspects 26-30, or a formulation according to any one of aspects 31-40.
42. The method of aspect 41, wherein the compound binds to the GnRH receptor in the mammal without stimulating GnRH activity.
43. The method of aspect 42, wherein the method is repeated until a physiological effect associated with administration of the compound occurs at a statistically significant level in a population of the mammals.
44. The method of aspect 43, wherein the method results in detectable suppression of luteinizing hormone (LH), follicle-stimulating hormone (FSH), or both in the mammal.
45. The method of aspect 44, wherein the mammal is a female and the method results in detectable decreases in the blood concentration of estradiol, progesterone, or both in the mammal.
46. The method of any one of aspects 41-45, wherein performance of the method detectably induces cytochrome P450 (CYP) 3A, detectably inhibits efflux transporter p-glycoprotein (P-gp), detectably binds to an organic anion transporting polypeptide (OATP), or results in the combination of any or all thereof.
47. The method of any one of aspects 41-46, wherein the mammal is a female and performance of the method detectably regulates oocyte maturation and/or ovulation.
48. The method of any one of aspects 41-47, wherein performance of the method detectably and significantly reduces gonadotrophin secretion in the mammal.
49. The method of any one of aspects 41-48, wherein the mammal is a human.
50. The method of aspect 49, wherein the human is a patient diagnosed as having or being at substantial risk of developing a disease or condition that is treatable or preventable by the method.
51. The method of aspect 50, wherein the method has been demonstrated to be effective for the treatment or prevention of the disease or condition in a statistically significant number of patients in at least one well-controlled and adequate (including adequately powered) clinical study.
52. The method of aspect 50 or aspect 51, wherein the patient is a woman receiving assisted reproductive technology and the application of the method increases the fertility rate in a significant proportion of a population of women in a well-controlled and adequate clinical study of promoting fertility and/or successful in vitro fertilization.
53. The method of aspect 52, wherein the method comprises administering a formulation according to any one of aspects 31-40 once a day to the patient.
54. The method of aspect 53, wherein the amount of compound administered once a day to the patient is about 25 mg to about 100 mg.
55. The method of aspect 54, wherein the method comprises repeating daily administration for up to 24 months.
56. The method of any one of aspects 53-55, wherein the patient is a female and has been diagnosed as suffering from moderate to severe endometriosis-associated pain and the method has been demonstrated to treat a statistically significant amount (i.e., number) of patients suffering from moderate to severe endometriosis-associated pain in at least one well-controlled and adequate clinical trial.
57. The method of any one of aspects 53-56, wherein the patient is a female and has been diagnosed as suffering from or being at risk of developing (e.g., substantial risk or imminent risk of developing) a uterine fibroid-related condition and the method has been demonstrated to treat a statistically significant amount of patients suffering from the uterine fibroid-related condition in at least one well-controlled and adequate clinical trial.
58. The method of any one of aspects 49-57, wherein the human patient is a female and has been diagnosed with dysmenorrhea (menstrual cramps) and performance of the method treats dysmenorrhea in the patient or has been demonstrated to treat dysmenorrhea in a statistically significant proportion of a population of patients in a well-controlled and adequate clinical study.
59. The method of any one of aspects 49-58, wherein the human patient is a female and has been diagnosed as suffering from non-menstrual pelvic pain (NMPP) and performance of the method treats NMPP in the patient or has been demonstrated to treat dysmenorrhea in a statistically significant proportion of a population of patients in a well-controlled and adequate clinical study.
60. The method of 49-51, wherein the human patient is a male and the method is used to treat prostate cancer, benign prostatic hyperplasia (enlarged prostate), or both.
61. The method of any one of aspects 49-60, wherein the mean AUC of the compound in one or more well-controlled and adequate clinical studies conducted with the formulation used in the method is at least about 1500 ng*h/mL.
62. The method of aspect 61, wherein the mean AUC of the compound in the one or more studies is at least 1800 ng*h/mL
63. The method of aspect 61 or aspect 62, wherein the accumulation for the compound in vivo is at least about 20% greater than the accumulation for once a day administration of the same amount of elagolix, and the clearance is at least about 20% lower than the clearance of once a day administration of the same amount of elagolix, or both.
64. The method of aspect 49, wherein the method comprises administering a formulation according to any one of aspects 31-40 twice a day to the patient.
65. The method of aspect 64, wherein the amount of the compound in each of the two daily administrations is about 50 mg to about 125 mg.

66. The method of aspect 65, wherein the patient is a female and has been diagnosed as suffering from endometriosis-associated pain and the method has been demonstrated to treat endometriosis-associated pain in at least one well-controlled and adequate clinical trial.
67. The method of aspect 66, wherein the endometriosis-pain comprises dyspareunia and the compound has been demonstrated to treat a statistically significant amount of patients suffering from endometriosis associated pain comprising dyspareunia in at least one well-controlled and adequate clinical trial.
68. The method of any one of aspects 64-67, wherein the patient is a female and has been diagnosed as suffering from or being at risk of developing (e.g., substantial risk or imminent risk of developing) a uterine fibroid-related condition and the method has been demonstrated to treat a statistically significant amount of patients suffering from the uterine fibroid-related condition in at least one well-controlled and adequate clinical trial.
69. The method of any one of aspects 64-68, wherein the mean AUC measured in at least one well-controlled and adequate study achieved by performance of the method is at least about 2000 ng*h/mL.
70. The method of aspect 69, wherein the mean AUC measured is at least about 2500 ng*h/mL.
71. The method of aspect 70, wherein the mean AUC measured is at least about 2750 ng*h/mL.
72. The method of any one of aspects 64-71, wherein the patient is a female diagnosed as suffering from dysmenorrhea (menstrual cramps) and the method comprises treating the dysmenorrhea or the method has been demonstrated to treat dysmenorrhea in at least one well-controlled and adequate clinical study.
73. The method of any one of aspects 64-72, wherein the patient is a female diagnosed as suffering from non-menstrual pelvic pain (NMPP) and the method comprises treating the NMPP or the method has been demonstrated to treat NMPP in at least one well-controlled and adequate clinical study.
74. The method of any one of aspects 64-65 or 69-71, wherein the patient is a male that has been diagnosed with prostate cancer or benign prostatic hyperplasia (enlarged prostate) and the method comprises treating the prostate cancer, benign prostatic hyperplasia, or both in the male patient or the method has been demonstrated to treat prostate cancer, benign prostatic hyperplasia, or both in at least one well-controlled and adequate clinical study.
75. The method of any one of aspects 64-65 or 69-71, wherein the patient is a female receiving assistive reproductive technology and performance of the method promotes fertilization in the female.
76. The method of any one of aspects 64-75, wherein the accumulation for the compound in vivo is at least about 20% greater than the accumulation for twice a day administration of the same amount of elagolix, the clearance is at least about 20% lower than the clearance of twice a day administration of the same amount of elagolix, or both.
77. The method of any one of aspects 64-73, and 75-76, wherein the patient is a female and the method is associated with a statistically significant reduction in hot flashes, night sweats, or both in patients in at least one well-controlled and adequate clinical study of the patients as compared to clinical data associated with elagolix.
78. The method of any one of aspects 49-59, 61-73, wherein the patient is a female and the method is associated with a statistically significant difference in the intensity and/or duration of menstrual bleeding in at least one well-controlled and adequate clinical study of the patients as compared to clinical data associated with elagolix.
79. The method of any one of aspects 49-78, wherein the method is associated with a statistically significant reduction in the occurrence of nausea in patients in at least one well-controlled and adequate clinical study of the patients as compared to clinical data associated with elagolix.
80. The method of any one of aspects 49-79, wherein the method is associated with a statistically significant difference in the amount of serum alanine aminotransferase (ALT) in patients in at least one well-controlled and adequate clinical study of the patients as compared to clinical data associated with elagolix.
81. The method of any one of aspects 49-80, wherein the occurrence of mood swings, depression, or similar condition is lower in a statistically significant proportion of a population receiving the method in at least one well-controlled and adequate study as compared to the clinical data for elagolix or direct comparison with elagolix (in a head-to-head study).
82. The method of any one of aspects 49-81, wherein the method is associated with a statistically significant difference in triglyceride levels, cholesterol levels, or both as compared with the clinical data for elagolix.
83. The compound of aspect 11, wherein at least 4 of R1, R2, R3, R4, R5, and R6 are deuterium.
84. The compound of aspect 83, wherein at least 5 of R1, R2, R3, R4, R5, and R6 are deuterium.
85. The compound of aspect 84, wherein all of R1, R2, R3, R4, R5, and R6 are deuterium.
86. The compound of any one of aspects 83-85, wherein at least one of H56, H57, and H58 are deuterium.
87. The compound of aspect 86, wherein two of H56, H57, and H58 are deuterium.
88. The compound of aspect 86, wherein all of H56, H57, and H58 are deuterium.
89. The compound of any one of aspects 83-85, wherein there are no deuterium atoms in the compound outside of positions R1, R2, R3, R4, R5, and R6.
90. The compound of aspect 89, wherein the compound is elagolix-d6.
91. A pharmaceutically acceptable salt of a compound according to any one of aspects 83-90.
92. A pharmaceutical formulation comprising a compound according to any of aspects 83-91 and one or more pharmaceutically acceptable excipients.
93. The formulation of aspect 92, wherein the formulation is formulated for oral administration to a human patient and comprises about 20-about 140 mg of the compound.
94. A method of modulating GnRH receptor activity in a mammal comprising administering an effective amount of a compound according to any one of aspects 83-90 to the mammal.
95. The method of aspect 94, wherein the method comprises once a day or twice a day administration of the compound for a period of at least one month, and optionally less than 36, 30, or 24 months.
96. The method of aspect 95, wherein the subject is a human female patient and has been diagnosed as suffering from moderate to severe endometriosis-associated pain and the method is performed to treat the same.
97. The method of aspect 96, wherein the method has been demonstrated to treat a statistically significant amount (i.e., number) of patients suffering from moderate to severe endometriosis-associated pain in at least one well-controlled and adequate clinical trial.
98. The method of aspect 95, wherein the subject is a human female patient and has been diagnosed as suffering from or being at risk of developing (e.g., substantial risk or imminent risk of developing) a uterine fibroid-related condition and the method is used to treat the same.
99. The method of aspect 95, wherein the subject is a female human patient and has been diagnosed with dysmenorrhea (menstrual cramps) and the performance of the method treats the same.
100. The method of aspect 94, wherein the subject is a human female patient is a female and has been diagnosed as suffering from non-menstrual pelvic pain (NMPP) and performance of the method treats the same.
101. The method of aspect 94, wherein the subject is a human male patient and the method is used to treat prostate cancer, benign prostatic hyperplasia (enlarged prostate), or both diagnosed in the male patient.
102. A method of modulating GnRH receptor activity in a human subject comprising orally administering about 40 mg to about 120 mg of a compound that modulates GnRH receptor activity in humans and which comprises a chemical structure according to the formula

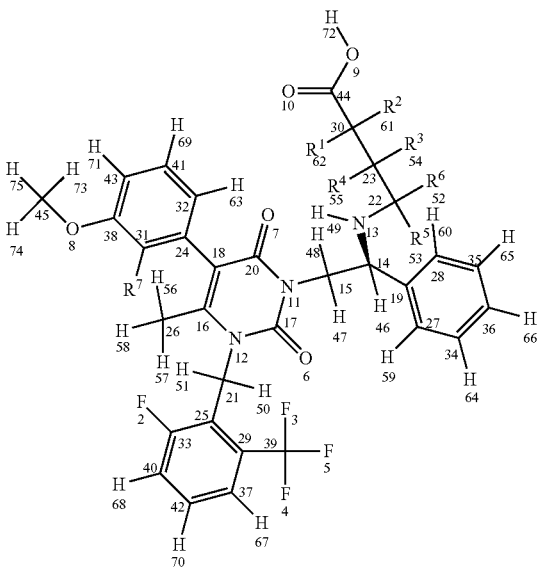

or a pharmaceutically acceptable salt thereof to the human subject, wherein (a) the compound comprises between 1-9 deuterium atoms; (b) R1, R2, R3, R4, R5, and R6 are either deuterium or hydrogen; (c) R7 is either fluorine or chlorine; and (c) at least one of the deuterium atoms is at a position selected from R1, R2, R3, R4, R5, and R6 or substitutes a hydrogen at position H73, H74, or H75.
103. The method of aspect 102, wherein the only deuterium atoms in the composition (a) are located a R1, R2, R3, R4, R5, and R6; (b) substitute hydrogens at position H73, H74, and H75; or (c) are located at positions that satisfy both (a) and (b).
104. The method of any one of aspect 102 or 103, wherein at least one of the deuterium atoms is located at position H73, H74, or H75 of the formula.
105. The method of any one of aspects 102-104, wherein at least two of the hydrogens at positions H73, H74, and H75 of the formula are substituted with deuterium.
106. The method of any one of aspects 102-105, wherein all of the hydrogens at positions H73, H74, and H75 of the formula are substituted with deuterium.
107. The method of any one of aspects 102-106, wherein the compound contains three deuterium atoms.
108. The method of any one of aspects 104-108, wherein only one or two of the hydrogens at positions H73, H74, and H75 of the formula are substituted with deuterium.
109. The method of any one of aspects 102-108, wherein the formulation comprises 60 mg-110 mg of the compound.
110. The method of any one of the aspects 102-108, wherein the formulation comprises 65 mg-105 mg of the compound.
111. The method of any one of aspects 102-108, wherein the formulation comprises administering the compound to the patient once or twice a day for at least some days during a treatment period of at least one month.
112. The method of aspect 111, wherein the treatment period lasts at least three months.
113. The method of aspect 112, wherein the treatment period lasts at least six months.
114. The method of aspect 111, wherein the compound is administered once daily at least some of the days of the treatment period.
115. The method of aspect 111, wherein the method comprises reducing the amount of compound administered, the frequency of administration, or both, during the treatment period.
116. The method of any one of aspects 102-108, wherein the human subject is a human female diagnosed as having or being at substantial risk of developing a condition selected from (a) endometriosis-associated pain, (b) a uterine fibroid-related condition; (c) dysmenorrhea; (d) non-menstrual pelvic pain; or (e) a combination of any or all of (a)-(d) and the method is performed to treat or prevent the condition.
117. The method of aspect 116, wherein the female has been diagnosed with endometriosis-associated pain and the method is performed to treat the pain.
118. The method of any one of aspects 102-108, wherein the human subject is a human male diagnosed with a condition selected from (a) prostate cancer; (b) benign prostatic hyperplasia; or (c) both prostate cancer and benign prostatic hyperplasia, and the method is performed to treat the condition.
119. A method of modulating GnRH receptor activity in a mammal comprising administering an effective amount of a compound according to aspect 6, wherein at least one of H56, H57, and H58 are substituted.
120. The method of aspect 119, wherein at least two of H56, H57, and H58 are substituted.
121. The method of aspect 120, wherein all three of H56, H57, and H58 are substituted.
122. The method of any one of aspects 119-121, wherein there are no deuterium atoms in the compound outside of those located at H56, H57, or H58.

123. The method of aspect 122, wherein the compound is elagolix-d3.
124. The method of any one of aspects 119-123, wherein the method comprises administering a pharmaceutically acceptable salt of the compound.
125. The method of any one of aspects 119-124, wherein the compound is formulated in a pharmaceutically acceptable formulation comprising one or more excipients for oral administration.
126. The method of any one of aspects 119-125, wherein the method comprises once a day or twice a day administration of the compound for a period of at least one month, and optionally less than 36, 30, or 24 months.
127. The method of aspect 126, wherein the subject is a human female patient and has been diagnosed as suffering from moderate to severe endometriosis-associated pain and the method is performed to treat the same.
128. The method of aspect 127, wherein the method has been demonstrated to treat a statistically significant amount (i.e., number) of patients suffering from moderate to severe endometriosis-associated pain in at least one well-controlled and adequate clinical trial.
129. The method of aspect 126, wherein the subject is a human female patient and has been diagnosed as suffering from or being at risk of developing (e.g., substantial risk or imminent risk of developing) a uterine fibroid-related condition and the method is used to treat the same.
130. The method of aspect 126, wherein the subject is a female human patient and has been diagnosed with dysmenorrhea (menstrual cramps) and the performance of the method treats the same.
131. The method of aspect 126, wherein the subject is a human female patient is a female and has been diagnosed as suffering from non-menstrual pelvic pain (NMPP) and performance of the method treats the same.
132. The method of aspect 126, wherein the subject is a human male patient and the method is used to treat prostate cancer, benign prostatic hyperplasia (enlarged prostate), or both diagnosed in the male patient.
133. The method of any one of aspects 119-132, wherein the method comprises administering about 20 mg to about 140 mg of the compound to the subject once per day or twice per day.
134. The method of aspect 133, wherein the method comprises administering about 40 mg to about 120 mg of the compound to the subject once per day or twice per day.
135. A pharmaceutical composition for oral administration comprising about 20 mg to about 140 mg of a compound according to aspect 6 wherein at least one of H56, H57, and H58 are substituted.
136. The composition of aspect 135, wherein at least two of H56, H57, and H58 in the compound are substituted.
137. The composition of aspect 136, wherein all three of H56, H57, and H58 in the compound are substituted.
138. The composition of any one of aspects 135-137, wherein there are no deuterium atoms in the compound outside of those located at H56, H57, or H58.
139. The composition of aspect 138, wherein the compound is elagolix-d3.
140. The composition of any one of aspects 135-139, wherein the composition comprises a pharmaceutically acceptable salt of any of the compounds described in such aspects.
141. The composition of any one of aspects 135-140, wherein the composition comprises about 20-about 120 mg of the compound.
142. The composition of aspect 141, wherein the composition comprises about 25-about 100 mg of the compound.
143. A method of treating endometriosis-associated pain in a human female patient comprising orally administering a pharmaceutically acceptable composition comprising a compound comprising a chemical structure according to the formula:

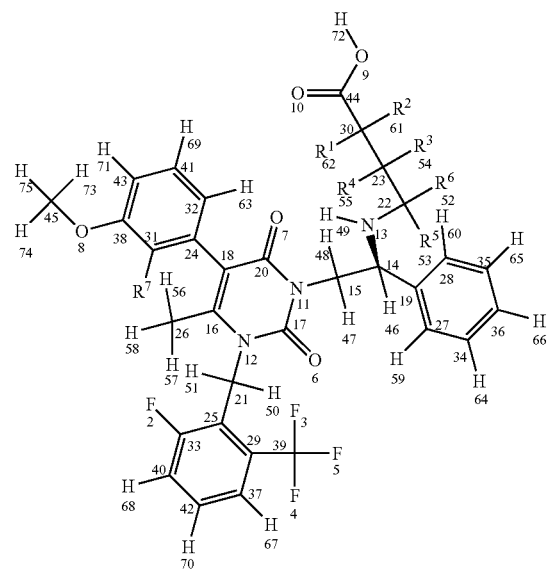

or a pharmaceutically acceptable salt thereof to the patient wherein (a) the compound comprises at least 1 deuterium atom; (b) R1, R2, R3, R4, and R6 are either deuterium or hydrogen; (c) R7 is either fluorine or chlorine; and (c) at least one of the deuterium atoms is at a position selected from R1, R2, R3, R4, R5, and R6 or substitutes a hydrogen at position H73, H74, or H75.
144. The method of aspect 143, wherein the compound comprises between 1-9 deuterium atoms.
145. The method of any one of aspects 143 or 144, wherein R7 is fluorine.
146. The method of any one of aspects 143-145, wherein the pharmaceutically acceptable composition comprises about 40 mg to about 120 mg of the compound.
147. The method of any one of aspects 143-146 wherein the only deuterium atom or atoms in the compound are located at R1, R2, R3, R4, R5, and R6 or substitute hydrogens at positions H73, H74, and H75.
148. The method of aspect 147, wherein at least two of H73, H74, and H75 are substituted with deuterium.
149. The method of aspect 148, wherein the method comprises administering the composition to the patient once daily or twice daily during at least a portion of a treatment period of at least one month.
150. The method of aspect 149, wherein the method comprises administering the composition to the patient once daily in at least some part of the treatment period.
151. The method of any one of aspects 149 or 150, wherein the method comprises administering about 60 mg to about 110 mg of the composition to the patient during at least some part of the treatment period.
152. The method of aspect 151, wherein all of the H73, H74, and H75 are substituted with deuterium.
153. The method of aspect 152, wherein the compound contains three deuterium atoms.
154. The method of claim 151, wherein the method comprises administering about 70 mg to about 105 mg of the composition to the patient during at least some part of the treatment period.
155. A pharmaceutically acceptable formulation for oral administration comprising less than about 150 mg of a compound that modulates GnRH receptor activity in human patients and which comprises a chemical structure according to the formula or a pharmaceutically acceptable salt thereof, wherein (a) the compound comprises at least one deuterium atom; (b) R1, R2, R3, R4, R5, and R6 are either deuterium or hydrogen; (c) R7 is either fluorine or chlorine; and (c) at least one of the deuterium atoms is at a position selected from R1, R2, R3, R4, R5, and R6 or substitutes a hydrogen at position H73, H74, or H75.
156. The formulation of aspect 155, wherein the compound comprises between 1-9 deuterium atoms.
157. The formulation of any one of aspects 155-156, wherein R7 is chlorine.
158. The formulation of any one of aspects 155-157, wherein the compound is present in an amount of between about 40 mg and about 120 mg.
159. The formulation of aspect 155, wherein the only deuterium atoms in the composition are located at R1, R2, R3, R4, R5, and R6 or substitute hydrogens at positions H73, H74, and H75 or exist both in one or more of positions R1, R2, R3, R4, R5, and R6 and substitute one or more hydrogens at positions H73, H74, and H75.
160. The formulation of aspect 156, wherein at least one of the deuterium atoms is located at position H73, H74, or H75.
161. The formulation of aspect 160, wherein at least two of the H73, H74, and H75 are substituted with deuterium.
162. The formulation of aspect 161, wherein all of the hydrogens in positions H73, H74, and H75 are substituted with deuterium.
163. The formulation of aspect 162, wherein the compound contains three deuterium atoms.
164. The formulation of any one of aspect 158, wherein one or two of the hydrogens at positions H73, H74, and H75 are substituted with deuterium.
165. The formulation according to any one of aspects 155-157 or aspects 159-164, wherein the formulation comprises 65 mg-105 mg of the compound.
166. A pharmaceutical formulation comprising 40 mg to 120 mg of the compound of any one of aspects 1-25.
167. The pharmaceutical formulation of aspect 166 formulated for oral administration.
168. A compound having a structure according to Formula I or a pharmaceutically acceptable salt thereof, wherein (a) R1, R2, R3, R4, R5, and R6 are either deuterium or hydrogen; (b) at least one of R1, R2, R3, R4, R5, and R6 is deuterium; (b) R7 is either fluorine or chlorine; and (c) the compound comprises between 1-9 deuterium atoms, wherein 0-8 of the hydrogen atoms in Formula I are substituted with deuterium.
169. The compound of aspect 168, wherein R7 is fluorine.
170. The compound of aspect 168 or aspect 169, wherein at least 75% of the 1-9 deuterium atoms in the compound are located at positions R1, R2, R3, R4, R5, or R6 or substitute a hydrogen at position H56, H57, H58, H73, H74, or H75.
171. The compound of aspect 170, wherein all of the 1-9 deuterium atoms in the compound are located at positions R1, R2, R3, R4, R5, or R6 or substitute a hydrogen at position H56, H57, H58, H73, H74, or H75.
172. The compound of aspect 171, wherein at least 75% of the 1-9 deuterium atoms are located at positions R1, R2, R3, R4, R5, or R6 or substitute a hydrogen at position H56, H57, or H58.
173. The compound of aspect 172, wherein the hydrogens at positions H73, H74, and H75 are maintained.

174. The compound of aspect 173, wherein all of the 1-9 deuterium atoms are located at positions R1, R2, R3, R4, R5, or R6 or substitute a hydrogen at position H56, H57, or H58.
175. The compound of aspect 174, wherein the compound comprises at least two deuterium atoms.
176. The compound of aspect 175, wherein the compound comprises at least four deuterium atoms, wherein at least one of the deuterium atoms substitute a hydrogen at position H56, H57, or H58.
177. The compound of aspect 176, wherein at least 2 of R1, R2, R3, R4, R5, and R6 are deuterium.
178. The compound of aspect 177, wherein at least 3 of R1, R2, R3, R4, R5, and R6 are deuterium.
179. The compound of aspect 178, wherein no more than two deuterium atoms substitute hydrogens at positions H56, H57, and H58.
180. The compound of any one of aspects 168-179, wherein the compound comprises no more than five deuterium atoms.
181. The compound of any one of aspects 168-179, wherein the compound contains 6-9 deuterium atoms.
182. The compound of aspect 181, wherein at least 4 of R1, R2, R3, R4, R5, and R6 are deuterium.
183. The compounds of aspect 182, wherein at least 5 of R1, R2, R3, R4, R5, and R6 are deuterium.
184. The compound of aspect 183, wherein all of R1, R2, R3, R4, R5, and R6 are deuterium.
185. The compound of aspect 184, wherein the compound contains 6-8 deuterium atoms.
186. The compound of aspect 185, wherein the compound contains 6-7 deuterium atoms.
187. The compound of aspect 186, wherein the compound contains 6 deuterium atoms.
188. A compound comprising a salt form of any one of the compounds of aspects 168-187.
189. The compound of aspect 188, wherein the compound is a sodium salt of a compound according to any one of aspects 168-187.
190. The compound of any one of aspects 168-189, wherein the compound has a half-life of about 6-about 12 hours in a human subject.
191. The compound of aspect 190, wherein the compound has a half-life of at least about 7 hours.
192. The compound of aspect 191, wherein the compound has an in vivo half-life of at least about 8 hours.
193. A composition comprising at least 1 mcg of a mixture of at least two isotopologues, wherein at least one of the at least two isotopologues is a compound according to any one of aspects 168-192.
194. The composition of aspect 193, wherein the average deuteration rate is at least about 75% in all positions in which a hydrogen is replaced by a deuterium.
195. The composition of aspect 194, wherein the average deuteration rate is at least about 95%.
196. The composition of aspect 195, wherein the average deuteration rate is at least 99%.
197. The composition of aspect 196, wherein the average deuteration rate is at least 99.5%.
198. A pharmaceutically acceptable formulation comprising a therapeutically effective amount of a compound according to any one of aspects 168-192 or a composition according to any one of aspects 193-197, and at least one pharmaceutically acceptable carrier, diluent, or excipient.
199. The formulation of aspect 198, wherein the formulation comprises about 25-250 mg of the compound or composition.
200. The formulation of aspect 199, wherein the formulation comprises about 35 mg to about 200 mg of the compound or composition.
201. The formulation of aspect 200, wherein the formulation comprises about 40 mg to about 150 mg of the compound or composition.
202. The formulation of aspect 201, wherein the formulation comprises about 50 mg to about 135 mg of the compound or composition.
203. The formulation of aspect 202, wherein the formulation comprises about 65 mg to about 130 mg of the compound or composition.
204. The formulation of aspect 203, wherein the formulation comprises about 75 mg, about 100 mg, or about 125 mg of the compound or composition.
205. The formulation of any one of aspects 198-204, wherein the formulation is in the form of a tablet for oral administration.
206. The formulation of aspect 205, wherein the formulation is stable at 2° C. to 30° C. for at least 24 months.
207. The formulation of aspect 206, wherein the formulation comprises three or more excipients selected from the group consisting of mannitol, sodium carbonate monohydrate, pregelatinized starch, povidone, magnesium stearate, polyvinyl alcohol, titanium dioxide, polyethylene glycol, and talc.
208. A method of modulating GnRH receptor activity comprising administering to a mammalian subject a physiologically effective amount of a compound according to any one of aspects 168-192, a composition according to any one of aspects 193-197, or a formulation according to any one of aspects 198-207.
209. The method of aspect 208, wherein the compound binds to the GnRH receptor in the mammal without stimulating GnRH activity.
210. The method of aspect 209, wherein the method is repeated until a physiological effect associated with administration of the compound occurs at a statistically significant level in a population of the mammals.
211. The method of aspect 210, wherein the method results in detectable suppression of luteinizing hormone (LH), follicle-stimulating hormone (FSH), or both in the mammal.
212. The method of aspect 211, wherein the mammal is a female and the method results in detectable decreases in the blood concentration of estradiol, progesterone, or both in the mammal.
213. The method of any one of aspects 209-212, wherein performance of the method detectably induces cytochrome P450 (CYP) 3A, detectably inhibits efflux transporter p-glycoprotein (P-gp), detectably binds to an organic anion transporting polypeptide (OATP), or results in the combination of any or all thereof.
214. The method of any one of aspects 209-213, wherein the mammal is a female and performance of the method detectably regulates oocyte maturation and/or ovulation.
215. The method of any one of aspects 209-214, wherein performance of the method detectably and significantly reduces gonadotrophin secretion in the mammal.
216. The method of any one of aspects 208-215, wherein the mammal is a human.
217. The method of aspect 216, wherein the human is a patient diagnosed as having or being at substantial risk of developing a disease or condition that is treatable or preventable by the method.
218. The method of aspect 217, wherein the method has been demonstrated to be effective for the treatment or prevention of the disease or condition in a statistically significant number of patients in at least one well-controlled and adequate (including adequately powered) clinical study.
219. The method of aspect 217 or aspect 218, wherein the patient is a woman receiving assisted reproductive technology and the application of the method increases the fertility rate in a significant proportion of a population of women in a well-controlled and adequate clinical study of promoting fertility and/or successful in vitro fertilization.
220. The method of aspect 219, wherein the method comprises administering a formulation according to any one of aspects 198-207 once a day to the patient.
221. The method of aspect 220, wherein the amount of compound administered once a day to the patient is about 25 mg to about 100 mg.
222. The method of aspect 221, wherein the method comprises repeating daily administration for up to 24 months.
223. The method of any one of aspects 220-222, wherein the patient is a female and has been diagnosed as suffering from moderate to severe endometriosis-associated pain and the method has been demonstrated to treat a statistically significant amount (i.e., number) of patients suffering from moderate to severe endometriosis-associated pain in at least one well-controlled and adequate clinical trial.
224. The method of any one of aspects 220-222, wherein the patient is a female and has been diagnosed as suffering from or being at risk of developing (e.g., substantial risk or imminent risk of developing) a uterine fibroid-related condition and the method has been demonstrated to treat a statistically significant amount of patients suffering from the uterine fibroid-related condition in at least one well-controlled and adequate clinical trial.
225. The method of any one of aspects 216-224, wherein the human patient is a female and has been diagnosed with dysmenorrhea (menstrual cramps) and performance of the method treats dysmenorrhea in the patient or has been demonstrated to treat dysmenorrhea in a statistically significant proportion of a population of patients in a well-controlled and adequate clinical study.
226. The method of any one of aspects 216-225, wherein the human patient is a female and has been diagnosed as suffering from non-menstrual pelvic pain (NMPP) and performance of the method treats dysmenorrhea in the patient or has been demonstrated to treat dysmenorrhea in a statistically significant proportion of a population of patients in a well-controlled and adequate clinical study.
227. The method of 216-218, wherein the human patient is a male and the method is used to treat prostate cancer, benign prostatic hyperplasia (enlarged prostate), or both.
228. The method of any one of aspects 216-227, wherein the mean AUC of the compound in one or more well-controlled and adequate clinical studies conducted with the formulation used in the method is at least about 1500 ng*h/mL.
229. The method of aspect 228, wherein the mean AUC of the compound in the one or more studies is at least 1800 ng*h/mL.
230. The method of aspect 228 or aspect 229, wherein the accumulation for the compound in vivo is at least about 20% greater than the accumulation for once a day administration of the same amount of elagolix, and the clearance is at least about 20% lower than the clearance of once a day administration of the same amount of elagolix, or both.
231. The method of aspect 219, wherein the method comprises administering a formulation according to any one of aspects 198-207 twice a day to the patient.
232. The method of aspect 231, wherein the amount of the compound in each of the two daily administrations is about 50 mg to about 125 mg.
233. The method of aspect 232, wherein the patient is a female and has been diagnosed as suffering from endometriosis-associated pain and the method has been demonstrated to treat endometriosis-associated pain in at least one well-controlled and adequate clinical trial.
234. The method of aspect 233, wherein the endometriosis-pain comprises dyspareunia and the compound has been demonstrated to treat a statistically significant amount of patients suffering from endometriosis associated pain comprising dyspareunia in at least one well-controlled and adequate clinical trial.
235. The method of any one of aspects 231-234, wherein the patient is a female and has been diagnosed as suffering from or being at risk of developing (e.g., substantial risk or imminent risk of developing) a uterine fibroid-related condition and the method has been demonstrated to treat a statistically significant amount of patients suffering from the uterine fibroid-related condition in at least one well-controlled and adequate clinical trial.
236. The method of any one of aspects 231-235, wherein the mean AUC measured in at least one well-controlled and adequate study achieved by performance of the method is at least about 2000 ng*h/mL.
237. The method of aspect 236, wherein the mean AUC measured is at least about 2500 ng*h/mL.
238. The method of aspect 237, wherein the mean AUC measured is at least about 2750 ng*h/mL.
239. The method of any one of aspects 231-238, wherein the patient is a female diagnosed as suffering from dysmenorrhea (menstrual cramps) and the method comprises treating the dysmenorrhea or the method has been demonstrated to treat dysmenorrhea in at least one well-controlled and adequate clinical study.
240. The method of any one of aspects 231-239, wherein the patient is a female diagnosed as suffering from non-menstrual pelvic pain (NMPP) and the method comprises treating the NMPP or the method has been demonstrated to treat NMPP in at least one well-controlled and adequate clinical study.

241. The method of any one of aspects 231-232 or 236-238, wherein the patient is a male that has been diagnosed with prostate cancer or benign prostatic hyperplasia (enlarged prostate) and the method comprises treating the prostate cancer, benign prostatic hyperplasia, or both in the male patient or the method has been demonstrated to treat prostate cancer, benign prostatic hyperplasia, or both in at least one well-controlled and adequate clinical study.

242. The method of any one of aspects 231-232 or 236-238, wherein the patient is a female receiving assistive reproductive technology and performance of the method promotes fertilization in the female.

243. The method of any one of aspects 231-242, wherein the accumulation for the compound in vivo is at least about 20% greater than the accumulation for twice a day administration of the same amount of elagolix, the clearance is at least about 20% lower than the clearance of twice a day administration of the same amount of elagolix, or both.

244. The method of any one of aspects 231-240, and 242-243, wherein the patient is a female and the method is associated with a statistically significant reduction in hot flashes, night sweats, or both in patients in at least one well-controlled and adequate clinical study of the patients as compared to clinical data associated with elagolix.

245. The method of any one of aspects 216-230, 225-237, and 239-240, wherein the patient is a female and the method is associated with a statistically significant difference in the intensity and/or duration of menstrual bleeding in at least one well-controlled and adequate clinical study of the patients as compared to clinical data associated with elagolix.

246. The method of any one of aspects 216-245, wherein the method is associated with a statistically significant reduction in the occurrence of nausea in patients in at least one well-controlled and adequate clinical study of the patients as compared to clinical data associated with elagolix.

247. The method of any one of aspects 216-246, wherein the method is associated with a statistically significant difference in the amount of serum alanine aminotransferase (ALT) in patients in at least one well-controlled and adequate clinical study of the patients as compared to clinical data associated with elagolix.

248. The method of any one of aspects 216-247, wherein the occurrence of mood swings, depression, or similar condition is lower in a statistically significant proportion of a population receiving the method in at least one well-controlled and adequate study as compared to the clinical data for elagolix or direct comparison with elagolix (in a head-to-head study).

249. The method of any one of aspects 216-248, wherein the method is associated with a statistically significant difference in triglyceride levels, cholesterol levels, or both as compared with the clinical data for elagolix.

250. A method of treating endometriosis-associated pain in a human female patient comprising orally administering a pharmaceutically acceptable composition comprising about 40-about 120 mg of a compound comprising a chemical structure according to the formula

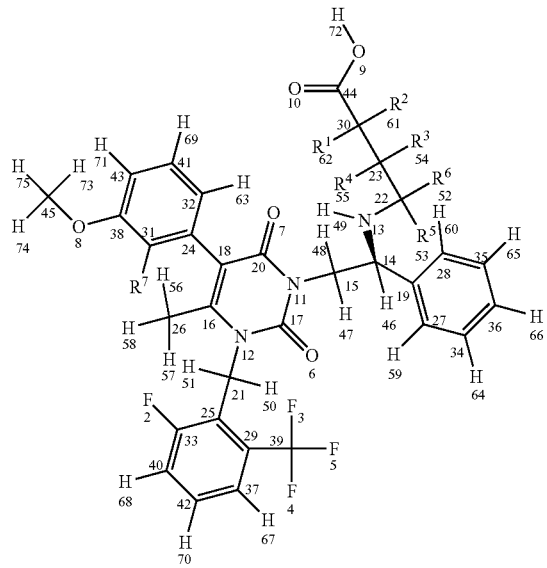

or a pharmaceutically acceptable salt thereof to the patient, wherein (a) the compound comprises between 1-9 deuterium atoms; (b) R1, R2, R3, R4, R5, and R6 are either deuterium or hydrogen; (c) R7 is either fluorine or chlorine; and (c) at least one of the deuterium atoms is at a position selected from R1, R2, R3, R4, R5, and R6 or substitutes a hydrogen at position H73, H74, or H75.

251. The method of aspect 250, wherein the only deuterium atoms in the compound (a) are located at R1, R2, R3, R4, R5, and R6; (b) substitute hydrogens at positions H73, H74, and H75; or (c) are located at positions that both satisfy (a) and (b).

252. The method of aspect 251, wherein at least one of the deuterium atoms in the compound is located at position H73, H74, or H75.

253. The method of aspect 252, wherein at least two of H73, H74, and H75 are substituted with deuterium.

254. The method of aspect 253, wherein the method comprises administering the composition to the patient once daily or twice daily during at least a portion of a treatment period of at least one month.

255. The method of aspect 254, wherein the method comprises administering the composition to the patient once daily in at least some part of the treatment period.

256. The method of aspect 254, wherein the method comprises administering about 60 mg-about 110 mg of the composition to the patient during at least some part of the treatment period.

257. The method of aspect 256, wherein all of H73, H74, and H75 are substituted with deuterium.

258. The method of aspect 257, wherein the compound contains three deuterium atoms.

259. The method of aspect 256, wherein the method comprises administering about 70 mg-about 105 mg of the composition to the patient during at least some part of the treatment period.

260. A pharmaceutically acceptable formulation for oral administration comprising about 40 mg to about 120 mg of a compound that modulates GnRH receptor activity in human patients and which comprises a chemical structure according to the formula

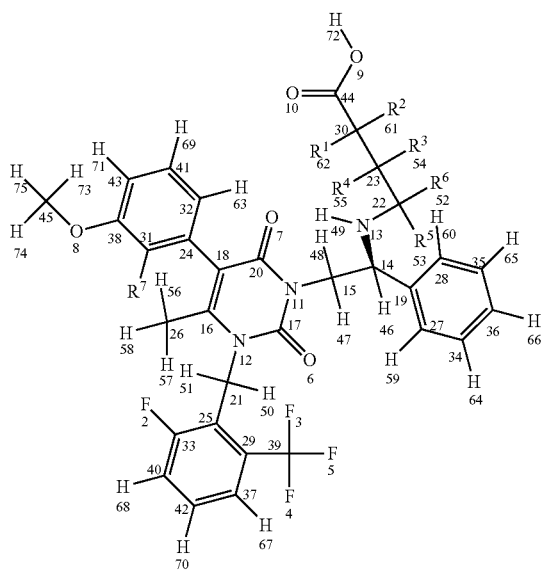

or a pharmaceutically acceptable salt thereof, wherein (a) the compound comprises between 1-9 deuterium atoms; (b) R1, R2, R3, R4, R5, and R6 are either deuterium or hydrogen; (c) R7 is either fluorine or chlorine; and (c) at least one of the deuterium atoms is at a position selected from R1, R2, R3, R4, R5, and R6 or substitutes a hydrogen at position H73, H74, or H75.

261. The formulation of aspect 260, wherein the only deuterium atoms in the composition (a) are located at R1, R2, R3, R4, R5, and R6; (b) substitute hydrogens at positions H73, H74, and H75; or (c) are located at positions that satisfy both (a) and (b).

262. The formulation of aspect 261, wherein at least one of the deuterium atoms is located at position H73, H74, or H75.

263. The formulation of aspect 262, wherein at least two of hydrogens at positions H73, H74, and H75 are substituted with deuterium.

264. The formulation of aspect 263, wherein all of the hydrogens at positions H73, H74, and H75 are substituted with deuterium.

265. A pharmaceutically acceptable compound comprising a structure according to the formula

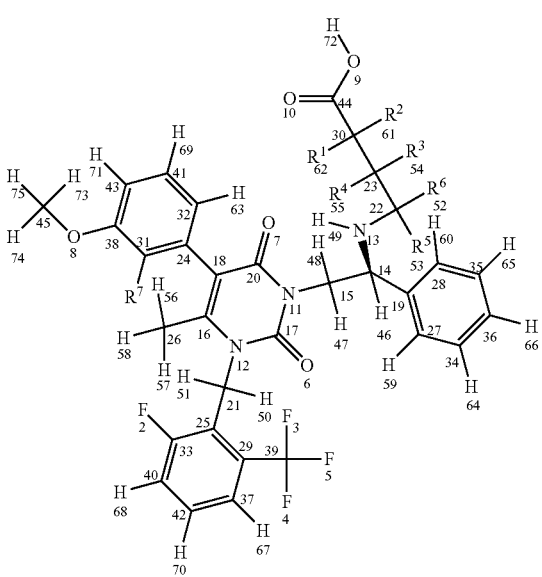

or a pharmaceutically acceptable salt thereof, wherein (a) the compound comprises between 1-11 deuterium atoms; (b) R1, R2, R3, R4, R5, and R6 are either deuterium or hydrogen; (c) R7 is either fluorine or chlorine; (d) at least one of the 1-11 deuterium atoms is located at a position selected from R1, R2, R3, R4, R5, and R6; and (e) at least one of H73, H74, and H75 is a hydrogen.

266. The compound of aspect 265, wherein the compound comprises at least two deuterium atoms and at least 75% of the 2-9 deuterium atoms in the compound are located at positions R1, R2, R3, R4, R5, or R6 or substitute a hydrogen at position H56, H57, H58, H73, H74, or H75.

267. The compound of aspect 266, wherein the hydrogens at positions H73, H74, and H75 of the formula are maintained.

268. The compound of aspect 267, wherein at least four of R1, R2, R3, R4, R5, and R6 are deuterium.

269. The compound of aspect 268, wherein all of R1, R2, R3, R4, R5, and R6 are deuterium.

270. A pharmaceutically acceptable formulation for oral administration comprising about 40 mg to about 120 mg of a compound that modulates GnRH receptor activity in human patients and which comprises a chemical structure according to the formula

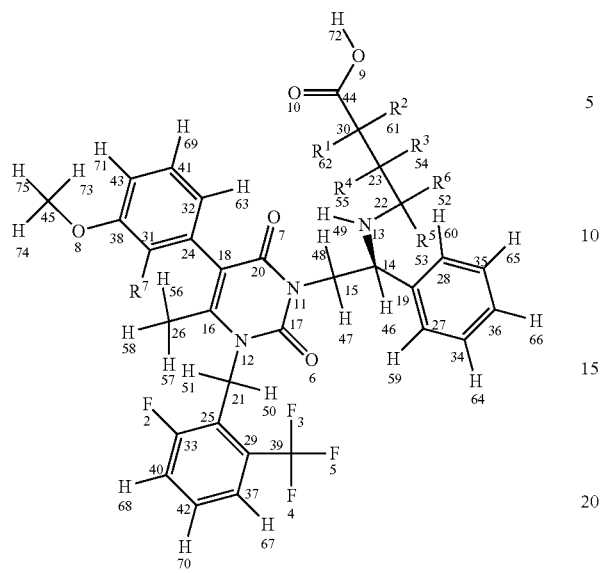

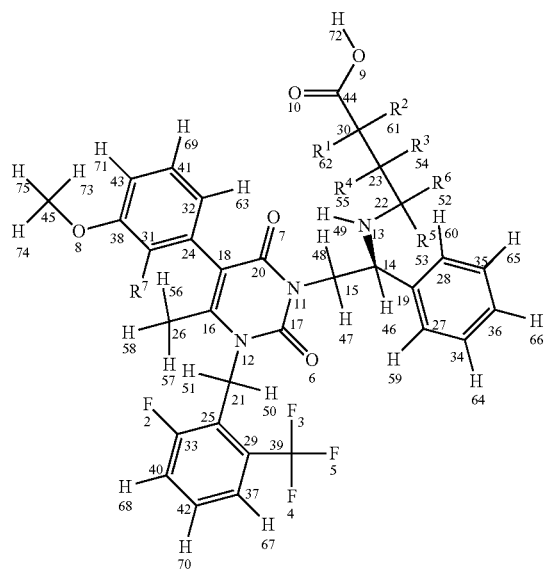

or a pharmaceutically acceptable salt thereof, wherein (a) the compound comprises between 1-9 deuterium atoms; (b) R1, R2, R3, R4, R5, and R6 are either deuterium or hydrogen; (c) R7 is either fluorine or chlorine; and (c) at least one of the deuterium atoms is at a position selected from R1, R2, R3, R4, R5, and R6 or substitutes a hydrogen at position H73, H74, or H75.

271. The formulation of aspect 270, wherein the only deuterium atoms in the composition (a) are located at R1, R2, R3, R4, R5, and R6; (b) substitute hydrogens at positions H73, H74, and H75; or (c) are located at positions that satisfy both (a) and (b).

272. The formulation of aspect 271, wherein at least one of the deuterium atoms is located at position H73, H74, or H75 of the formula.

273. The formulation of aspect 272, wherein at least two of hydrogens at positions H73, H74, and H75 of the formula are substituted with deuterium.

274. The formulation of aspect 273, wherein all of the hydrogens at positions H73, H74, and H75 of the formula are substituted with deuterium.

275. The formulation of aspect 274, wherein the compound contains three deuterium atoms.

276. The formulation of aspect 270, wherein one or two of the hydrogens at positions H73, H74, and H75 of the formula are substituted with deuterium.

277. A formulation according to any one of aspects 270-276, wherein the formulation comprises 60 mg-110 mg of the compound.

278. The formulation of aspect 277, wherein the formulation comprises 65 mg-105 mg of the compound.

279. A method of modulating GnRH receptor activity in a human subject comprising orally administering 40 mg to 120 mg of a compound that modulates GnRH receptor activity in humans and which comprises a chemical structure according to the formula or a pharmaceutically acceptable salt thereof to the human subject, wherein (a) the compound comprises between 1-9 deuterium atoms; (b) R1, R2, R3, R4, R5, and R6 are either deuterium or hydrogen; (c) R7 is either fluorine or chlorine; and (c) at least one of the deuterium atoms is at a position selected from R1, R2, R3, R4, R5, and R6 or substitutes a hydrogen at position H73, H74, or H75.

280. The method of aspect 279, wherein the hydrogens at positions H56, H57, and H58 of the formula are maintained.

281. The method of aspect 280, wherein the only deuterium atoms in the composition (a) are located at R1, R2, R3, R4, R5, and R6; (b) substitute hydrogens at positions H73, H74, and H75; or (c) are located at positions that satisfy both (a) and (b).

282. The method of aspect 281, wherein at least one of the deuterium atoms is located at position H73, H74, or H75 of the formula.

283. The method of aspect 282, wherein at least two of the hydrogens at positions H73, H74, and H75 of the formula are substituted with deuterium.

284. The method of aspect 283, wherein all of the hydrogens at positions H73, H74, and H75 of the formula are substituted with deuterium.

285. The method of aspect 283, wherein the compound contains three deuterium atoms.

286. The method of aspect 281, wherein only one or two of the hydrogens at positions H73, H74, and H75 of the formula are substituted with deuterium.

287. The method of any one of aspects 279-286, wherein the formulation comprises 60 mg-110 mg of the compound.

288. The method of any one of aspects 279-286, wherein the formulation comprises 65 mg-105 mg of the compound.

289. The method of any one of aspects 279-286, wherein the method comprises administering the compound to the patient once or twice a day for at least some days during a treatment period of at least one month.

290. The method of aspect 289, wherein the treatment period lasts at least three months.

291. The method of aspect 290, wherein the treatment period lasts at least six months.

292. The method of aspect 289, wherein the compound is administered once daily at least some of the days of the treatment period.

293. The method of aspect 289, wherein the method comprises reducing the amount of compound administered, the frequency of administration, or both, during the treatment period.

294. The method of any one of aspects 279-286, wherein the human subject is a human female diagnosed as having or being at substantial risk of developing a condition selected from (a) endometriosis-associated pain, (b) a uterine fibroid-related condition; (c) dysmenorrhea; (d) non-menstrual pelvic pain; or (e) a combination of any or all of (a)-(d) and the method is performed to treat or prevent the condition.

295. The method of aspect 294, wherein the female has been diagnosed with endometriosis-associated pain and the method is performed to treat the pain.

296. The method of any one of aspects 279-286, wherein the human subject is a human male diagnosed with a condition selected from (a) prostate cancer; (b) benign prostatic hyperplasia; or (c) both prostate cancer and benign prostatic hyperplasia, and the method is performed to treat the condition.

297. A pharmaceutically acceptable compound comprising a structure according to the formula

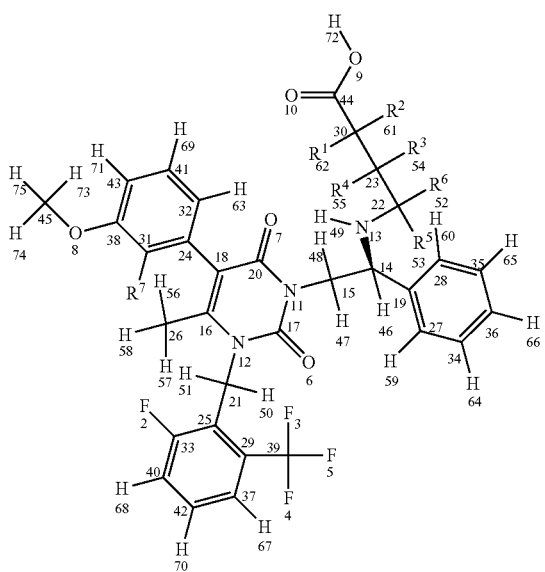

or a pharmaceutically acceptable salt thereof, wherein (a) the compound comprises between 1-11 deuterium atoms; (b) R1, R2, R3, R4, R5, and R6 are either deuterium or hydrogen; (c) R7 is either fluorine or chlorine; (d) at least one of the 1-11 deuterium atoms is located at a position selected from R1, R2, R3, R4, R5, and R6; and (e) at least one of H73, H74, and H75 is a hydrogen.

298. The compound of aspect 297, wherein R7 is fluorine.

299. The compound of aspect 298, wherein the compound comprises at least two deuterium atoms and at least 75% of the 2-11 deuterium atoms in the compound are located at positions R1, R2, R3, R4, R5, or R6 or substitute a hydrogen at position H56, H57, H58, H73, H74, or H75.

300. The compound of aspect 299 wherein all of the deuterium atoms in the compound are (a) located at one or more positions selected from R1, R2, R3, R4, R5, and R6; (b) substitute a hydrogen at position H56, H57, H58, H73, H74, or H75; or (c) are located at positions that satisfy some or all of both (a) and (b).

301. The compound of any one of aspects 297-300, wherein the hydrogens at positions H73, H74, and H75 are maintained.

302. The compound of any one of aspects 297-300, wherein one or two of the deuterium atoms substitute a hydrogen at position H56, H57, or H58.

303. The compound of any one of aspects 297-300, wherein at least two of R1, R2, R3, R4, R5, and R6 are deuterium.

304. The compound of aspect 303, wherein at least four of R1, R2, R3, R4, R5, and R6 are deuterium.

305. The compound of aspect 304, wherein all of R1, R2, R3, R4, R5, and R6 are deuterium.

306. The compound of aspect 305, wherein the compound contains six deuterium atoms.

307. The compound of aspect 305, wherein one or two of the hydrogens at positions H56, H57, and H58 of the formula are substituted with deuterium.

308. A pharmaceutical formulation formulated for oral administration comprising 40 mg to 120 mg of a compound according to any one of aspects 297-300.

309. A pharmaceutical formulation comprising 40 mg to 120 mg of a compound according to aspect 308.

310. A pharmaceutical formulation comprising 60 mg to 110 mg of a compound according to aspect 309.

The invention claimed is:

1. A method of treating endometriosis-associated pain in a human female patient comprising orally administering a pharmaceutically acceptable composition in a total daily dose comprising about 40-about 120 mg of a compound comprising a chemical structure according to the formula

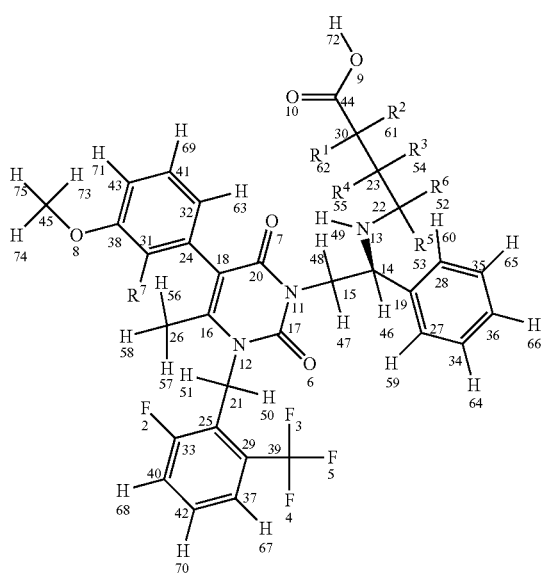

or a pharmaceutically acceptable salt thereof to the patient, wherein (a) the compound comprises between 1-9 deuterium atoms; (b) R1, R2, R3, R4, R5, and R6 are either deuterium or hydrogen; (c) R7 is either fluorine or chlorine; and (d) at least one of the deuterium atoms is at a position selected from R1, R2, R3, R4, R5, and R6 and at least one of the deuterium atoms substitutes a hydrogen at position H73, H74, or H75.

2. The method of claim 1, wherein the only deuterium atoms in the compound (a) are located at R1, R2, R3, R4, R5, and R6; (b) substitute hydrogens at positions H73, H74, and H75; or (c) are located at positions that both satisfy (a) and (b).

3. The method of claim 1, wherein at least two of H73, H74, and H75 are substituted with deuterium atoms.

4. The method of claim 3, wherein the method comprises administering the composition to the patient once daily or twice daily during at least a portion of a treatment period of at least one month.

5. The method of claim 4, wherein the method comprises administering the composition to the patient once daily in at least some part of the treatment period.

6. The method of claim 4, wherein the method comprises administering a total daily dose of about 60 mg-about 110 mg of the composition to the patient during at least some part of the treatment period.

7. The method of claim 6, wherein all of H73, H74, and H75 are substituted with deuterium atoms.

8. The method of claim 7, wherein the compound contains 4-9 deuterium atoms.

9. The method of claim 6, wherein the method comprises administering a total daily dose of about 70 mg-about 105 mg of the composition to the patient during at least some part of the treatment period.

10. The method of claim 1, wherein the compound comprises a deuterium atom substitution at only one of H73, H74, and H75.

11. The method of claim 1, wherein the compound comprises between 2-6 deuterium atoms located at positions R1, R2, R3, R4, R5, and R6.

12. The method of claim 11, wherein the compound comprises between 2-5 deuterium atoms located at positions R1, R2, R3, R4, R5, and R6.

13. The method of claim 11, wherein the compound comprises deuterium atoms at each of positions R1, R2, R3, R4, R5, and R6.

14. The method of claim 1 wherein R7 is chlorine.

15. A pharmaceutically acceptable compound comprising a structure according to the formula or a pharmaceutically acceptable salt thereof, wherein (a) the compound comprises between 1-12 deuterium atoms; (b) R7 is either fluorine or chlorine; (c) at least one of the 1-12 deuterium atoms is located at a position selected from R1, R2, R3, R4, R5, and R6; and (d) (I) at least one of R1, R2, R3, R4, R5, and R6 is a hydrogen, or (II) at least one of H73, H74, H56, H57, and H58 is a deuterium atom.

16. The compound of claim 15, wherein the compound comprises at least two deuterium atoms, and at least 75% of the 2-12 deuterium atoms in the compound are located at positions R1, R2, R3, R4, R5, or R6 or substitute a hydrogen at position H56, H57, H58, H73, H74, or H75.

17. The compound of claim 16, wherein at least one of the hydrogens at positions H73, H74, and H75 of the compound is substituted with a deuterium atom.

18. The compound of claim 17, wherein two of the hydrogens at positions H73, H74, and H75 of the compound are substituted with a deuterium atom.

19. The compound of claim 17, wherein all of the hydrogens at positions H73, H74, and H75 of the compound are substituted with a deuterium atom.

20. The compound of claim 15, wherein all of the hydrogens at positions H73, H74, and H75 of the compound are maintained.

21. The compound of claim 16, wherein at least one of the hydrogens at positions H56, H57, and H58 of the compound is substituted with a deuterium atom.

22. The compound of claim 21, wherein two of the hydrogens at positions H56, H57, and H58 of the compound are substituted with a deuterium atom.

23. The compound of claim 21, wherein all of the hydrogens at positions H56, H57, and H58 of the compound are substituted with a deuterium atom.

24. The compound of claim 15, wherein all of the hydrogens at positions H56, H57, and H58 of the compound are maintained.

25. The compound of claim 15, wherein at least two of R1, R2, R3, R4, R5, and R6 are deuterium atoms.

26. The compound of claim 25, wherein 2-5 of R1, R2, R3, R4, R5, and R6 are deuterium atoms.

27. The compound of claim 26, wherein all of R1, R2, R3, R4, R5, and R6 are deuterium atoms.

28. A pharmaceutically acceptable composition comprising a therapeutically effective amount of a compound of claim 15 and a pharmaceutically acceptable carrier.

29. A pharmaceutically acceptable composition comprising a therapeutically effective amount of a compound of claim 17 and a pharmaceutically acceptable carrier.

30. A pharmaceutically acceptable composition comprising a therapeutically effective amount of a compound of claim 19 and a pharmaceutically acceptable carrier.

31. A pharmaceutically acceptable composition comprising a therapeutically effective amount of a compound of claim 21 and a pharmaceutically acceptable carrier.

32. A pharmaceutically acceptable composition comprising a therapeutically effective amount of a compound of claim 23 and a pharmaceutically acceptable carrier.

33. A pharmaceutically acceptable composition comprising a therapeutically effective amount of a compound of claim 25 and a pharmaceutically acceptable carrier.

34. A pharmaceutically acceptable composition comprising a therapeutically effective amount of a compound of claim 26 and a pharmaceutically acceptable carrier.

35. A pharmaceutically acceptable composition comprising a therapeutically effective amount of a compound of claim 27 and a pharmaceutically acceptable carrier.

* * * * *